United States Patent [19]
Grek et al.

[11] Patent Number: 6,097,488
[45] Date of Patent: Aug. 1, 2000

[54] METHOD AND APPARATUS FOR MEASURING MICRO STRUCTURES, ANISOTROPY AND BIREFRINGENCE IN POLYMERS USING LASER SCATTERED LIGHT

[75] Inventors: Boris Grek, Santa Clara; Joseph Bartolick, Livermore, both of Calif.; Alan D. Kennedy, Wilmington, Del.

[73] Assignee: Princeton University, Princeton, N.J.

[21] Appl. No.: 09/102,254

[22] Filed: Jun. 22, 1998

[51] Int. Cl.[7] .................................................... G01J 4/00
[52] U.S. Cl. ........................................ 356/364; 356/365
[58] Field of Search ..................... 356/364, 365, 356/369, 370, 445; 250/339.11, 338.1

[56] References Cited

U.S. PATENT DOCUMENTS

| | | | |
|---|---|---|---|
| 4,140,902 | 2/1979 | Young | 250/225 |
| 4,668,860 | 5/1987 | Anthon | 250/225 |
| 4,887,155 | 12/1989 | Masson | 358/107 |
| 5,015,867 | 5/1991 | Siegel et al. | 250/560 |
| 5,257,092 | 10/1993 | Noguchi et al. | 356/367 |
| 5,264,909 | 11/1993 | Rochester | 356/73.1 |
| 5,365,067 | 11/1994 | Cole et al. | 250/341.8 |
| 5,443,610 | 8/1995 | Urruti | 65/486 |
| 5,619,325 | 4/1997 | Yoshida | 356/351 |

*Primary Examiner*—Frank G. Font
*Assistant Examiner*—Michael P. Stafira
*Attorney, Agent, or Firm*—Wolff & Samson

[57] ABSTRACT

A method and apparatus for measuring microstructures, anistropy and birefringence in polymers using laser scattered light includes a laser which provides a beam that can be conditioned and is directed at a fiber or film which causes the beam to scatter. Backscatter light is received and processed with detectors and beam splitters to obtain data. The data is directed to a computer where it is processed to obtain information about the fiber or film, such as the birefringence and diameter. This information provides a basis for modifications to the production process to enhance the process.

22 Claims, 21 Drawing Sheets

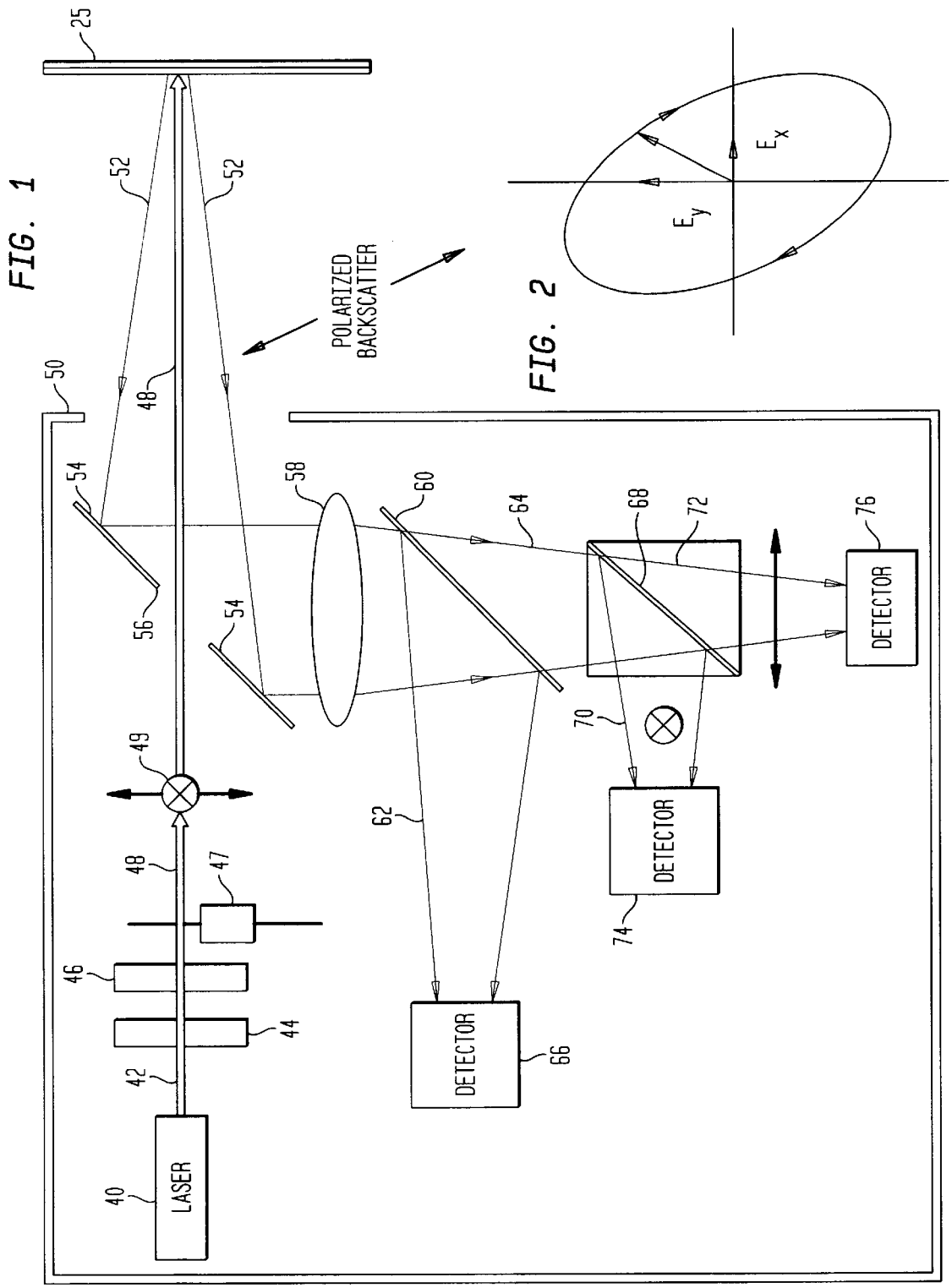

FIG. 12
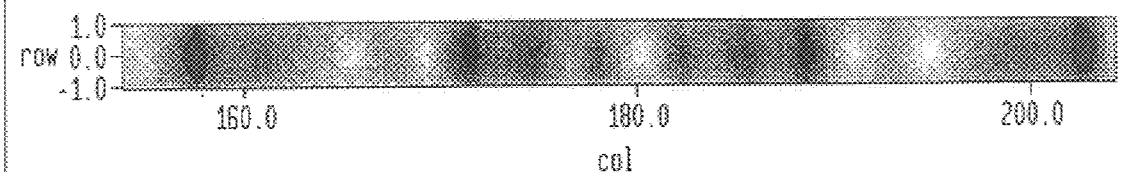
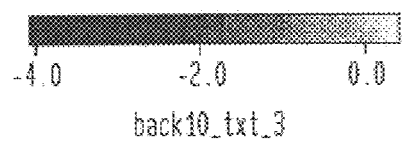
back10_txt_3
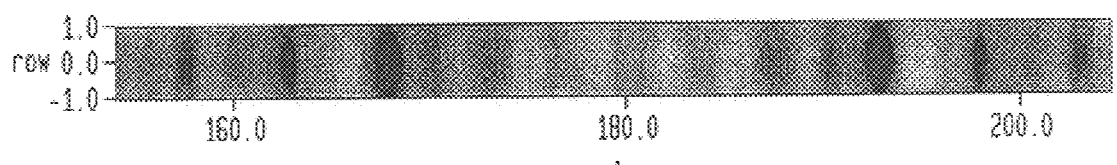
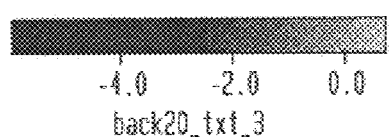
back20_txt_3
FIG. 13
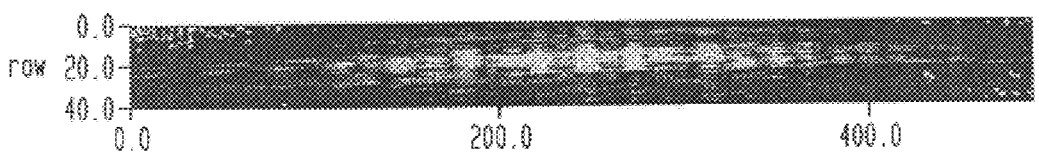
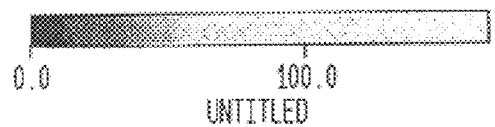
UNTITLED

METHOD AND APPARATUS FOR MEASURING MICRO STRUCTURES, ANISOTROPY AND BIREFRINGENCE IN POLYMERS USING LASER SCATTERED LIGHT

GOVERNMENT RIGHTS

The present invention has been made under the contract with the Department of Energy and the government may have certain rights to the subject invention.

BACKGROUND OF THE INVENTION

1. Field of the Invention

The present invention relates to a method and apparatus for measuring molecular alignment and crystallinity of polymer fibers and films, and more particularly to a method and apparatus for measuring diameter, and birefringence of fibers in real time during production.

2. Related Art

In the field of synthetic fiber and film manufacturing, it is desirable to measure the molecular alignment, or crystallinity, of polymer fibers and films to determine the degree of solidification, or other characteristics of the fiber, at a particular time. When a fiber or film is created at a factory, it is drawn or stretched, which tends to orient the crystals. The fiber has an index of refraction across the length of the fiber and has another index of refraction along the length of the fiber. The difference between these indices of refraction is the birefringence of the fiber. The birefringence is a good indicator of the degree of crystallinity or degree of orientation of the crystals comprising the fiber. It is highly desirable to determine the birefringence of a fiber or a film during the production process while it is moving from a liquid state to a solid state. In the past, the only way to obtain such a measurement, has been to halt the manufacturing process, obtain a sample of the fiber or film and perform off-line analysis in a laboratory, where the fiber or film is immersed in calibrated oils until it disappears, which means the index of refraction of the surrounding material is equal to the index of refraction of the fiber. This is an expensive and time consuming process, and is very disruptive to the manufacturing process. Another problem is that a plurality of fibers are drawn from a spinner, which looks like a shower head, so it is impossible to position equipment in front and behind a particular fiber.

Accordingly, what is desired, and has not been heretofore developed, is a method and apparatus for measuring microstructures, anisotropy and birefringence in fibers and films during the production in real time, without interrupting the manufacturing process.

Previous attempts in this area include the following:

Massen, U.S. Pat. No. 4,887,155, which discloses a method of measuring or monitoring properties of yarns using an image sensor to obtain a two-dimensional image of a portion of the yarn which is converted to an electrical image signal. The signal is digitized and the values of the properties to be detected are determined.

Siegel et al., U.S. Pat. No. 5,015,867, discloses a method and apparatus for measuring the diameter of a moving fiber using lasers and charged coupled devices for sensing the diffraction and interference patterns produced when electromagnetic radiation emitted from a laser is partially obscured by the edges of the strand. Information contained in the diffraction pattern may be extracted in a number of ways such as, for example, comparing the measured diffraction pattern with a theoretical pattern produced by a knife edge as calculated using the Kirchhoff-Fresnel integral.

Noguchi, et al., U.S. Pat. No. 5,257,092, discloses a polarization and birefringence measuring device utilizing a wide polarized light beam to impinge on a specimen. A photo detecting sensor detects the light beam containing information about the specimen. An analyzer is used to vary the amount of light transmitted. A computer analyzes the polarization states of parts of the specimen corresponding to the samples taken.

Rochester, U.S. Pat. No. 5,264,909, discloses a method and apparatus for measuring the diameter of an optical fiber as the fiber moves past the measuring apparatus. The device includes a number of discreet, stationery light sensors arranged in a linear array, a light source positioned to shine a beam of light onto the sensors of the array and a lens that directs an enlarged image of the optical fiber onto the array of light sensors. Each light sensor produces an output signal responsive to the intensity of light it receives.

Urruti, U.S. Pat. No. 5,443,610, discloses an apparatus for controlling fiber diameter by taking two measurements of the fiber diameter and combining the measurements into a control signal. The first measurement is made on the bare fiber and the second measurement is made after a hermetic coating has been applied to the fiber.

Ducharme, et al., U.S. Pat. No. 5,657,126, discloses an ellipsometer having a phase-modulated polarized light beam which is applied to a sample. Electric signals are obtained representing the orthogonal planes of polarization after the light has interacted with the sample and the constants of the sample are calculated from the two resulting electric signals.

Yoshita, U.S. Pat. No. 5,619,325, discloses an ellipsometry optical system for analyzing light beams reflected from or transmitted through materials. The device includes a light source, a beam splitter, an optical frequency shifter for shifting a frequency of one of the light beams split by the beam splitter to form a reference light beam, a circular polarization converter for circularly polarizing the other light beam to form a probing light beam, a second beam splitter for combining the reference beam and the probing beam, a birefringence prism for receiving the combined beam and separating polarization components and a photo detector for converting the polarization components to electrical signals.

None of these previous efforts, taken either alone or in combination, teach or suggest all of the elements of the present invention, nor do they disclose all of the benefits and advantages of the present invention.

OBJECTS AND SUMMARY OF THE INVENTION

It is a primary object of the present invention to measure the alignment and crystallinity of polymer fibers during the production thereof in real time.

It is another object of the present invention to measure the birefringence of fibers and/or in real time to determine properties of fibers or films during the manufacturing process.

It is still an additional object of the present invention to use lasers to measure properties of fibers during the manufacturing process.

It is still an additional object of the present invention to utilize laser light scattered by textile fibers during the manufacturing process to determine characteristics of the fibers.

It is still an additional object of the present invention to direct lasers at moving fibers to scatter the laser light to form an interference pattern which is dependent upon the diameter of the fiber and the orientation and structure of the polymer molecules within the fiber, and to obtain information about orientation and structure of the fiber.

It is even an additional object of the present invention to analyze the interference pattern of laser light scattered by fibers to determine the degree and nature of alignment of polymer chains and other physical characteristics of the fiber, including strength, elasticity and surface smoothness.

It is an additional object of the present invention to utilize information obtained in real time about textile fibers to allow process adjustments to be made immediately during production allowing for improved process reproducibility, efficiency and quality control and eliminating the need to overproduce to ensure adequate supply of fiber with consistent characteristic.

It is, accordingly, another object of the present invention to provide an improved textile production process with increased reproducibility, efficiency and quality control.

It is another object of the present invention to save money associated with the halting of the manufacturing process for testing.

It is an additional object of the present invention to overcome the need to test products off line in laboratories.

A method and apparatus for measuring microstructures, anistropy and birefringence in fibers using laser scattered light includes a laser which provides a beam that can be conditioned and is directed at a fiber or film which causes the beam to scatter. Backscatter light is received and processed with detectors and beam splitters to obtain data. The data is directed to a computer where it is processed to obtain information about the fiber or film, such as the birfringence. This information provides a basis for modifications to the production process to enhance the process.

BRIEF DESCRIPTION OF THE DRAWINGS

Other important objects and features of the invention will be apparent from the following Detailed Description of the Invention when read in context with the accompanying drawings in which:

FIG. 1 is a schematic drawing of an apparatus for determining birefringence according to the present invention.

FIG. 2 is a graph of the components of the ellipticity polarized backscattered laser light.

FIG. 12 shows a backscatter pattern from 10 micron filament and backscatter patterns for 20 micron filament.

FIG. 13 shows a typical backscatter pattern for an A1 fiber.

DETAILED DESCRIPTION OF THE INVENTION

Figure 3:
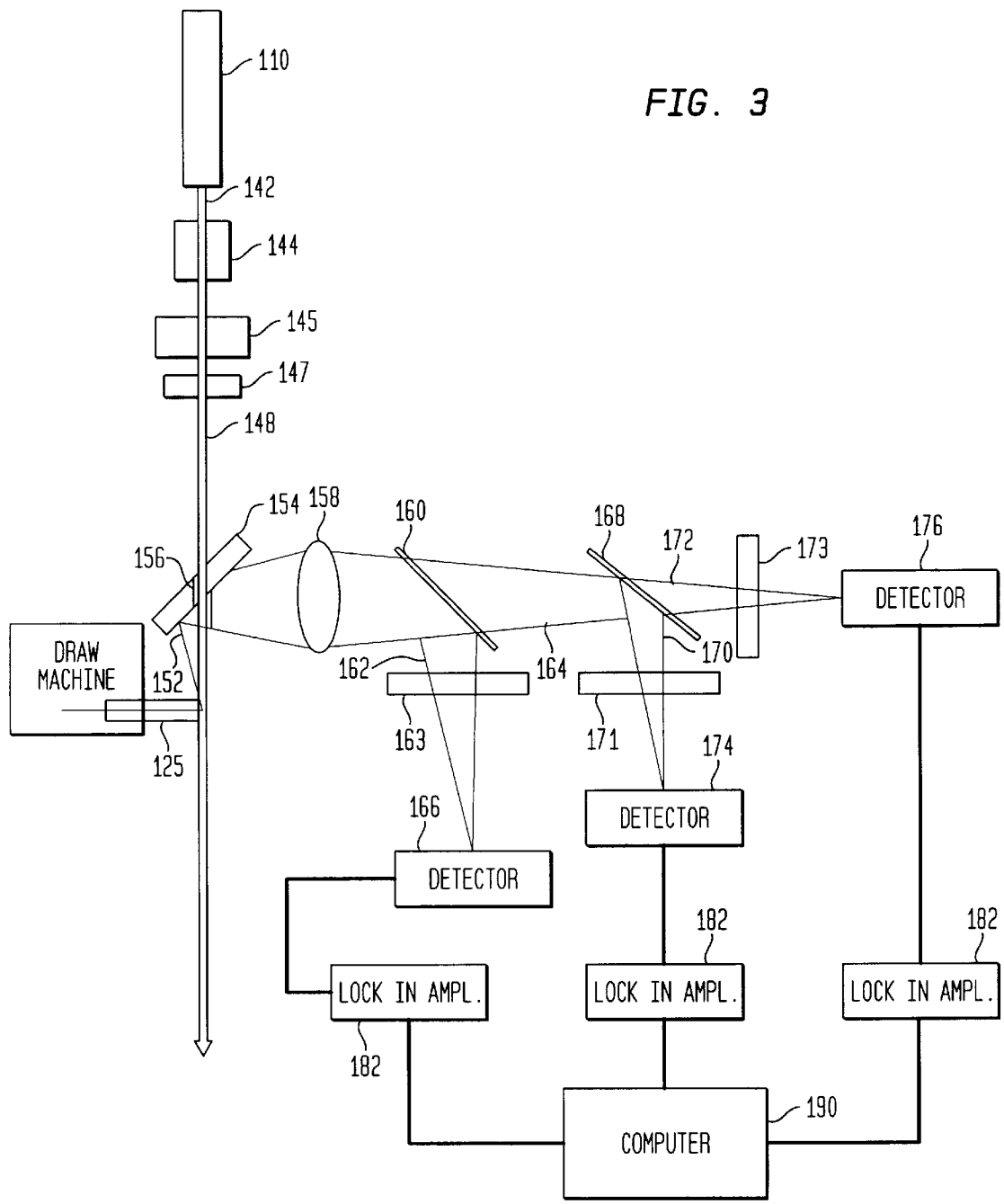
FIG. 3 is a schematic drawing of another embodiment of the apparatus shown in FIG. 1.

The present invention utilizes laser scattered light for measuring microstructures, anistropy and birefringence in fibers and films. Importantly, the method and apparatus of the present invention allows for the measurements of such properties in fibers and films during the production process in real time. Accordingly, process adjustments can be made during the production process to increase the efficiency of the process and increase the quality of the product.

Lasers operating in the infrared, visible and ultraviolet wavelength ranges can be used to monitor physical characteristics of synthetic fibers in accordance with the present invention. The laser light is directed at and scattered by the textile fibers during and immediately following the solidification of the extruded fibers and during the drawing process.

Two classes of measurements can be undertaken: a passive measurement and an active measurement. In the passive case, low-power laser light in the visible or near infrared frequency range is scattered by the moving fiber, forming an interference pattern which is dependent upon the diameter of the fiber and the orientation and structure of the polymer molecules within the fiber. The degree and nature of alignment of polymer chains is related to physical characteristics of the fiber, including strength, elasticity and surface smoothness. The greater the degree of the alignment, the stronger the fiber. The lesser the degree of the alignment, the greater the elasticity. Periodic variations in the structure of the polymer chain in the direction of the fiber movement can also be gleaned from changes in the scattering patterns with time, indicating changes in fiber properties. These changes can be caused by mechanical wobble, which if uncorrected, could render the fiber useless.

In the active case, light from the powerful infrared or ultraviolet lasers incident on the fiber is absorbed by the molecules and readmitted at a different wavelength. Spectroscopic analysis of the scattered light yields additional information on the chemical and physical composition of the fiber material. This allows manufacturers to control and maintain the chemical consistency of the product and related properties such as dye distribution and concentration.

In the factory, fibers are drawn out of a spinneret which includes a plurality of apertures through which the liquid is drawn. Because of this configuration, one cannot isolate a particular fiber and install equipment in front of and behind a typical analysis. Accordingly, the present invention utilizes the backscatter component of the laser beam on a fiber, i.e. that portion of the scattered light that is directed back at the laser beam, i.e., 180 degrees backscatter. A mirror can be used to obtain the backscatter which can be then analyzed to determine the product of the birefringence times the diameter of the fiber.

Referring to FIG. 1, an embodiment of the basic apparatus of the present invention is shown schematically. The device includes a housing 30 which houses a laser 40. The laser can be any type of laser known in the art such as a laser that operates in the infrared, visible or ultraviolet wavelength range. One suitable type of laser would be a helium neon laser.

The laser 40 emits a laser beam 42. The laser beam 42 is conditioned by polarization elements 44 and 46. The polarizers may be glass or acilinide that may have special coatings depending upon the wavelength. A chopper 47 may be utilized to modulate the beam by imposing a frequency on the laser beam 42. The polarized laser beam 48, the polarization of which is indicated by polarization symbol 49, is sent through aperture 56 of mirror 54 and out of the housing, through housing aperture 50. A portion of the polarized laser beam 48 is backscattered at 180 degrees, and this backscattered beam 52 comes back towards the aperture 50 and the housing 30 and passes through the aperture 50 and contacts mirror 54. The mirror 54 reflects the backscattered beam 52 through lens 58, and through some optical elements such as beam splitter 60 which separates the beams into first component 62 and second component 64. First component 62 is directed to a detector 66. The second component 64 passes through a second beam splitter 68 where it is split into third beam 70 and fourth beam 72. The third beam 70 is directed to second detector 74 and fourth beam 72 is directed to third detector 76.

Because the polarized beam has an elliptical polarization, it generally takes three detectors to determine the ellipticity of the light. See FIG. 2. The ellipticity of the light is proportional to the product of the birefringence and the diameter of the fiber. The detectors can be any desired detectors. For a helium laser, it may be desirable to use photo voltaic cells. Lock-in amplifiers interconnected with the detectors can be used to take modulated signal and filter out the noise, i.e., a very narrow band filter. Thereafter, the data is fed to a computer which analyzes the data as will hereinafter be discussed.

Importantly, it is desirable to position the laser to impact against the fiber at 45 degrees to obtain the most information, and accordingly, the controlling computer program must periodically check to determine that the apparatus maintains its position at 45 degrees with respect to the fiber which may move and or change as it is being drawn. It should also be noted that two independent measurements of the birefringence are necessary in order to get information and accordingly, two laser beams of two different wavelengths are required.

Referring now to FIG. 3, which is another embodiment of the invention shown in FIG. 1, like numerals represent like elements. A laser generally indicated at 140 emits a laser beam 142 which passes through a polarizer 144, a liquid crystal retarder 145, and an achromatic ¼ (one quarter) wave plate 147. The conditioned beam 148 is directed through an aperture 156 in a mirror 154 to contact a fiber 125 being from a drawing machine. The conditioned, beam then scatters causing a backscattered beam 152 which contacts the mirror 154 and is reflected to a horizontal lens 158 which directs the beam to first beam splitter 160 which splits the beam into two parts, the first part of which 162 passes through a polarizer 163 to a detector 166. The second part of the beam 164 is directed to another beam splitter 168 which splits the beam into two parts, third beam 170 which passes through a polarizer 171 which directs the beam to detector 174 and fourth beam 172 which passes through polarizer 173 to third detector 176. Lock-in amplifiers 182 are interconnected with the detectors 166, 174 and 176 respectively, and the resulting signals are sent to computer 190 for processing.

Scattering Patterns

The method of interpretation of the data by the computer results from experimental observations from a number of models. Most polymer filaments are at least partially transparent and have a high refractive index and refraction is expected to be the dominant effect. A forward scattered pattern is typical of such filaments. The pattern is banded and band position and period depend on filament shape, size and index of refraction. Most of the rays that generate the pattern have sampled most of the filament volume and therefore carry line integrated information on the dielectric constants of the sample and could be used as the basis of birefringence measurements. Single filaments were illuminated with monochromatic radiation from an He—Ne laser and the scattering pattern was sampled using a 2D CCD detector.

Figure 4:
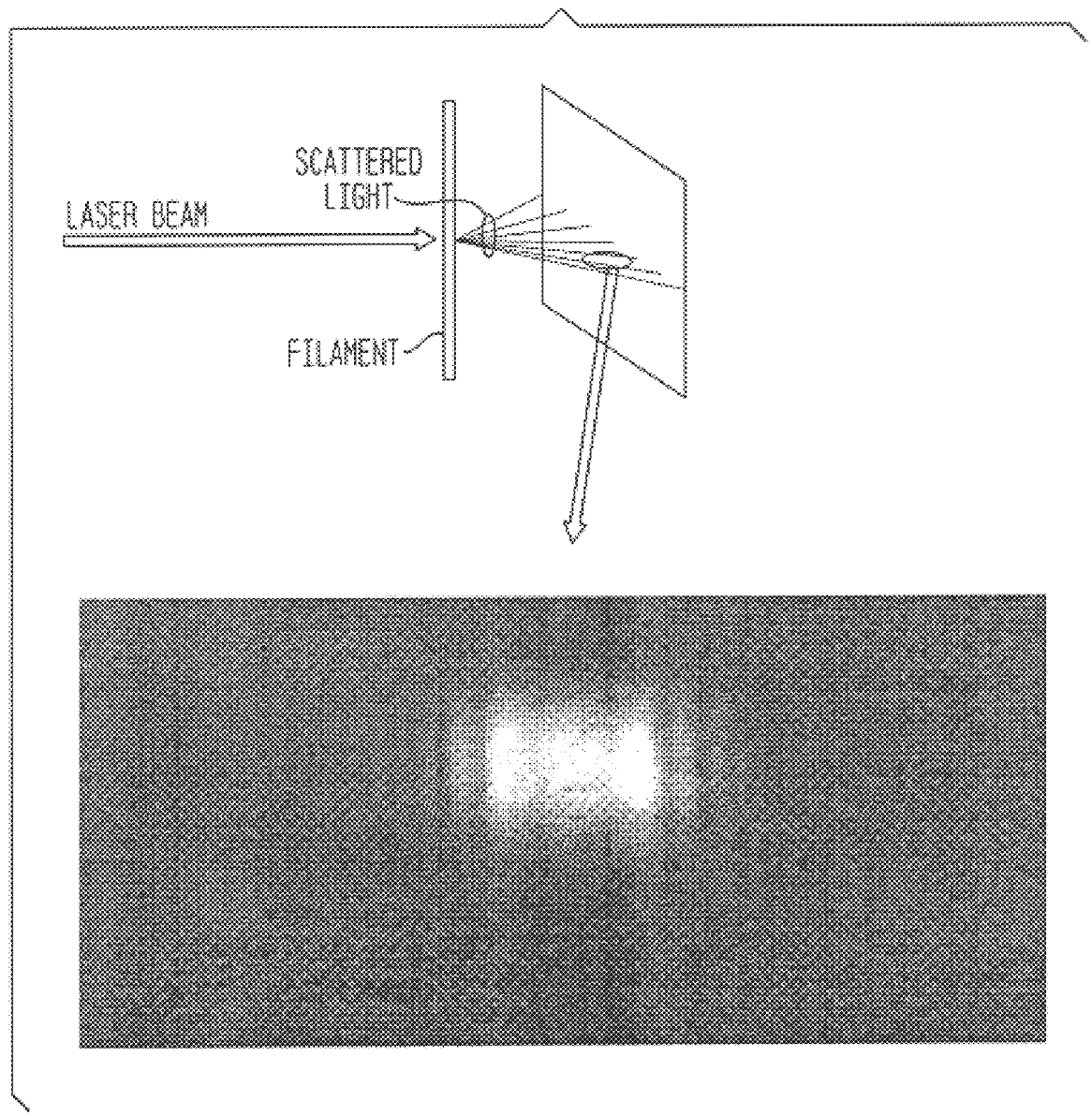
FIG. 4 shows a schematic for obtaining a scattered pattern through a filament, and the pattern obtained.

FIG. 4 shows the dominant pattern of light transmitted and refracted through a deeply pigmented nylon filament (Camac Nylon/Navy Blue). This forward scattered pattern is typical of all the filaments tested. The pattern is banded and band position and period depend on filament shape, size and index of refraction. Most of the rays that generate this pattern have sampled most of the filament volume. They therefore carry line integrated information on the dielectric constants of the sample and can be used as the basis of birefringence measurements.

Figure 5:
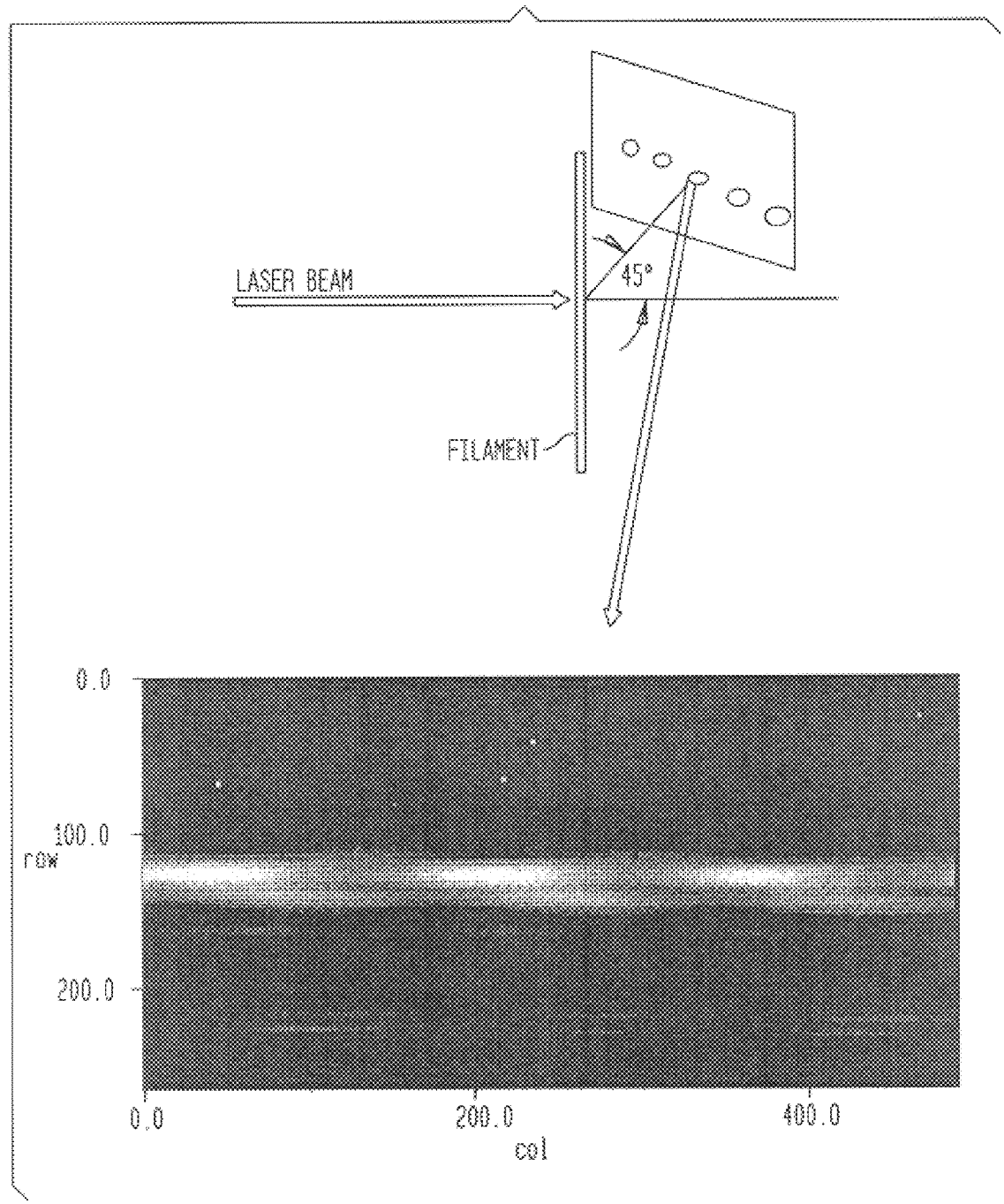
FIG. 5 shows a schematic for obtaining a scattered pattern at an angle and the scatter pattern.
Figure 6:
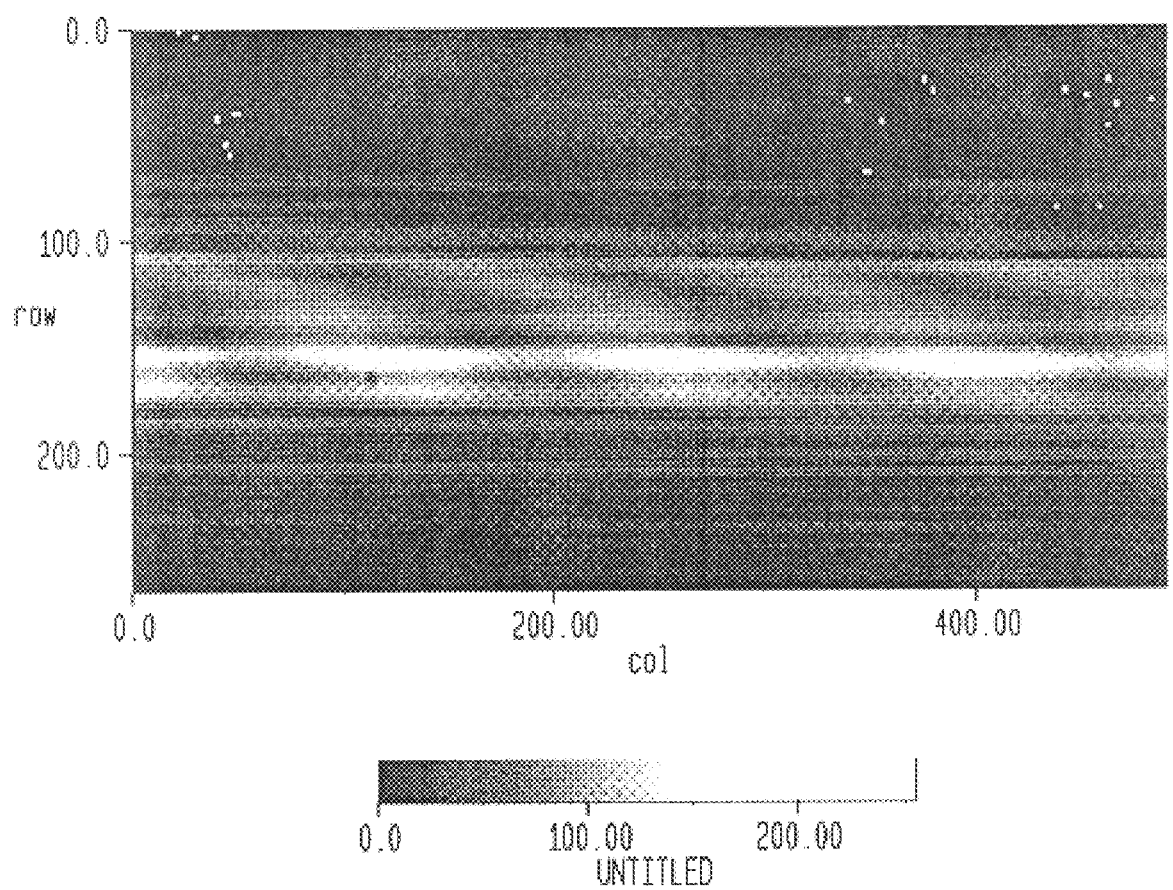
FIG. 6 shows a scattering pattern at a 45 degrees.

FIGS. 5 and 6 show the weaker equatorial patterns generated at other scattering angles. As will be discussed later, these are of the form expected from diffraction effects and cannot be calculated from simple ray tracing. The period of the spot pattern depends primarily on the filament diameter. The amplitude (intensity) and position of the spots depend on index of refraction of the filament. The vertical height of the spots reflects the diameter of the probing laser beam. An unexpected feature is the distortion in the spot and the sidebands that appear above and below the primary spots.

A more characteristic patter is shown in FIG. 6. There is considerably more structure in these patterns. The additional bands indicate inhomogeneities along the axis of the filament. The larger the separation from the primary spot structure the finer the structure. As an approximate guide, the horizontal separation in the primary spots can be used as a ruler to estimate the size of the inhomogeneities along the filament axis. The bands in FIG. 6 indicate the existence of inhomogeneities along the filament axis; their size is of the order of filament diameter.

Figure 7:
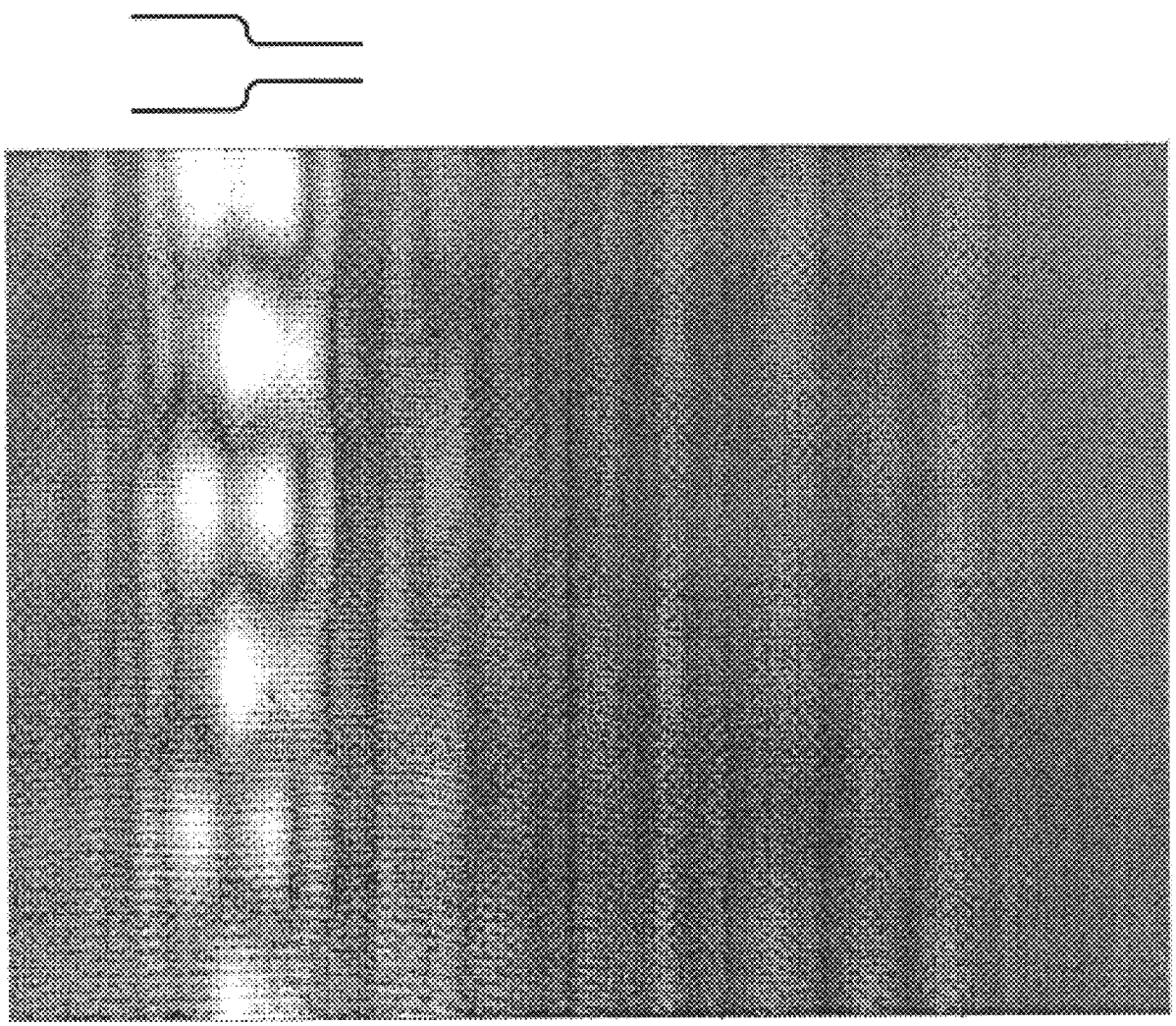
FIG. 7 shows a scattering pattern at 45 degrees from a necked fiber.

FIG. 7 shows the scattering pattern from a necked fiber. The position and separation of the dominant spots is representative of the neck ratio and neck length.

Figure 8:
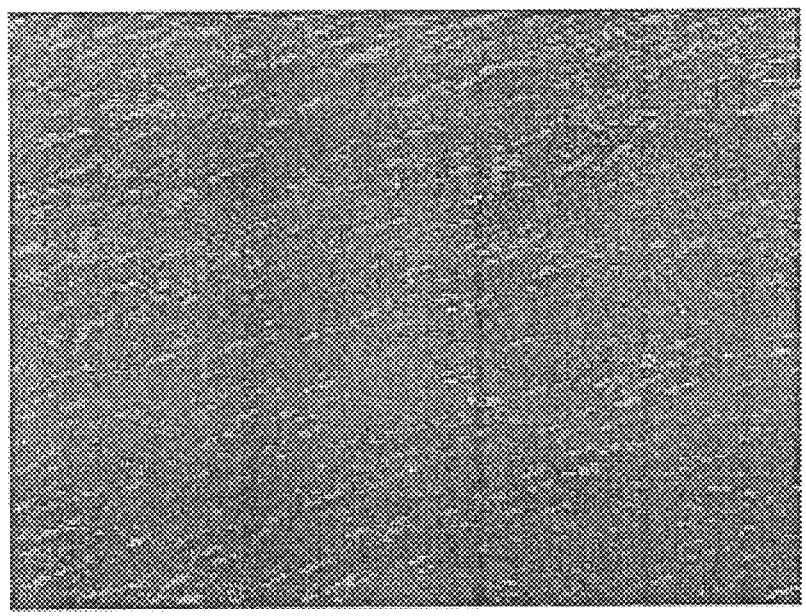
FIG. 8 shows a large angle scattering pattern for Camac Navy undrawn filament.
Figure 9:
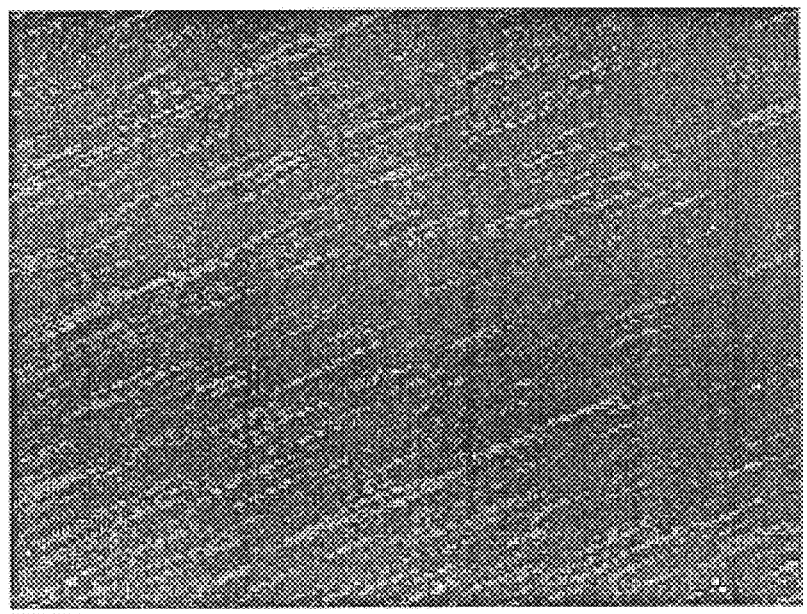
FIG. 9 shows a large angle scattering pattern for Camac Navy drawn filaments.

At small scattering angle the patterns stem from large morphological features with a size scale similar to the probing wavelength. At large angles, they carry information on structures with size of the order of a small fraction of the wavelength of the probing radiation. The regular spot pattern due to the filament diameter and gross inhomogeneities no longer appears at wide angles. Wide angle patterns of drawn and undrawn nylon filaments at 45 degrees in the azimuthal plane and at 25 degrees in the equatorial plane, are shown in FIGS. 8 and 9. These patterns are also characteristic of those from PET fibers. Fibers with high crystallinity and higher birefringence show a more coherent structure as indicated in the figures.

Fundamental Models

Ray Tracing and Fraunhoffer Diffraction Models

Figure 10:
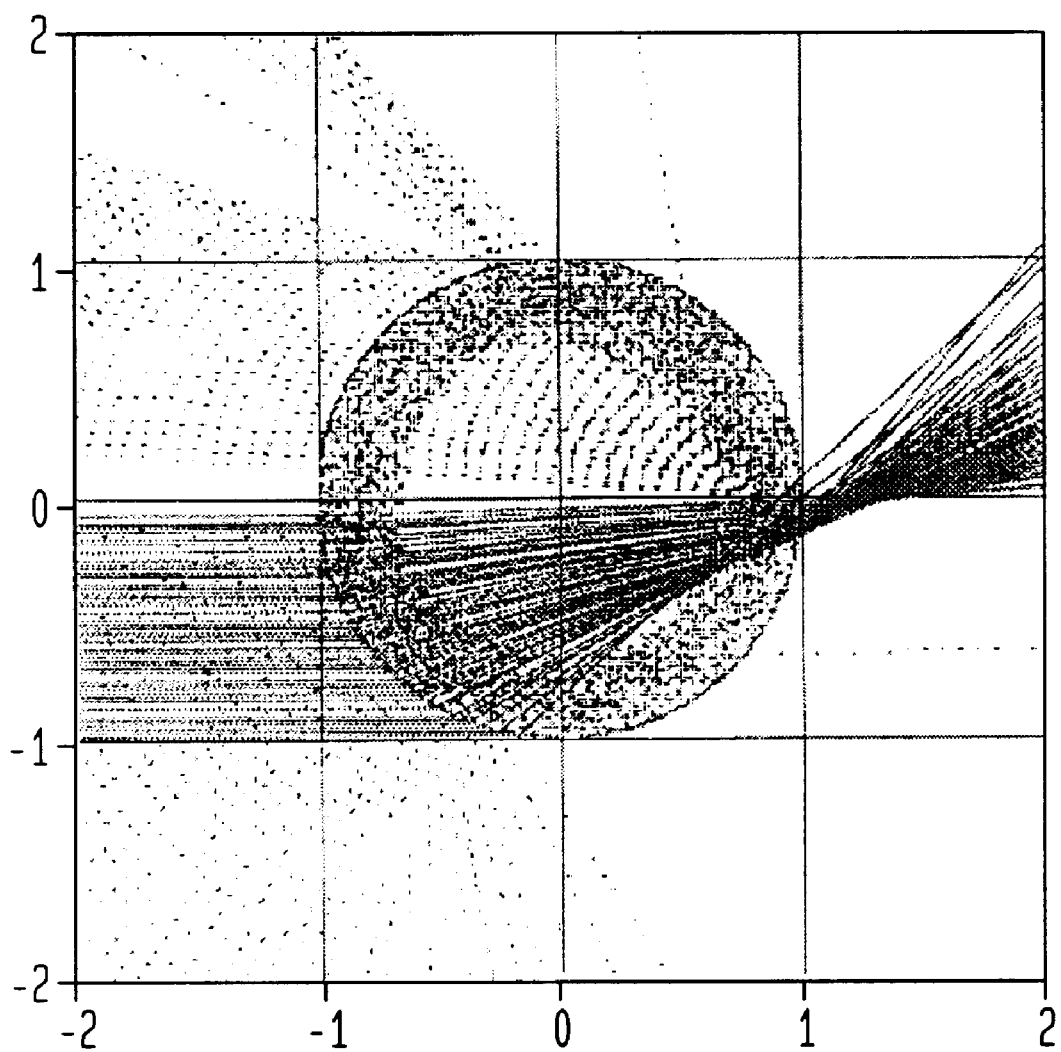
FIG. 10 shows a ray path diagram for rays instant on a fiber.

Ray tracing is the logical first step in trying to understand the scattering patterns. The result of such a calculation is shown in FIG. 10. For clarity only ray paths incident from below the mid-plane are plotted. The results shown are independent of the actual filament diameter and depend only on the index of refraction. The light is incident from the left of the image; an index of refraction of 1.5 was assumed. The dotted lines below the mid-plane are rays reflected from the front of the filament whereas the rays in the upper mid-plane are rays reflected from the back side of the filament. The fuzz that appears just inside the filament are rays that are trapped inside the filament. Ray tracing calculations are useful to estimate the path length a particular light ray has taken. Brightness patterns of the reflected and transmitted light can be determined by calculating the ray density at the position of interest. From FIG. 10 it is evident that all of these patterns will be smooth and cannot reproduce any of the banded patterns observed.

Diffraction effects must be included to reproduce the observed banded patterns. Several diffraction models were tested. All were able to generate spot patterns similar to FIG. 5. The diffraction models allowed determination of the filament diameter to better than 5% accuracy. They did not however accurately reproduce the amplitude or exact position of the dominant spot pattern.

Solution of Maxwell's Equations

Figure 11:
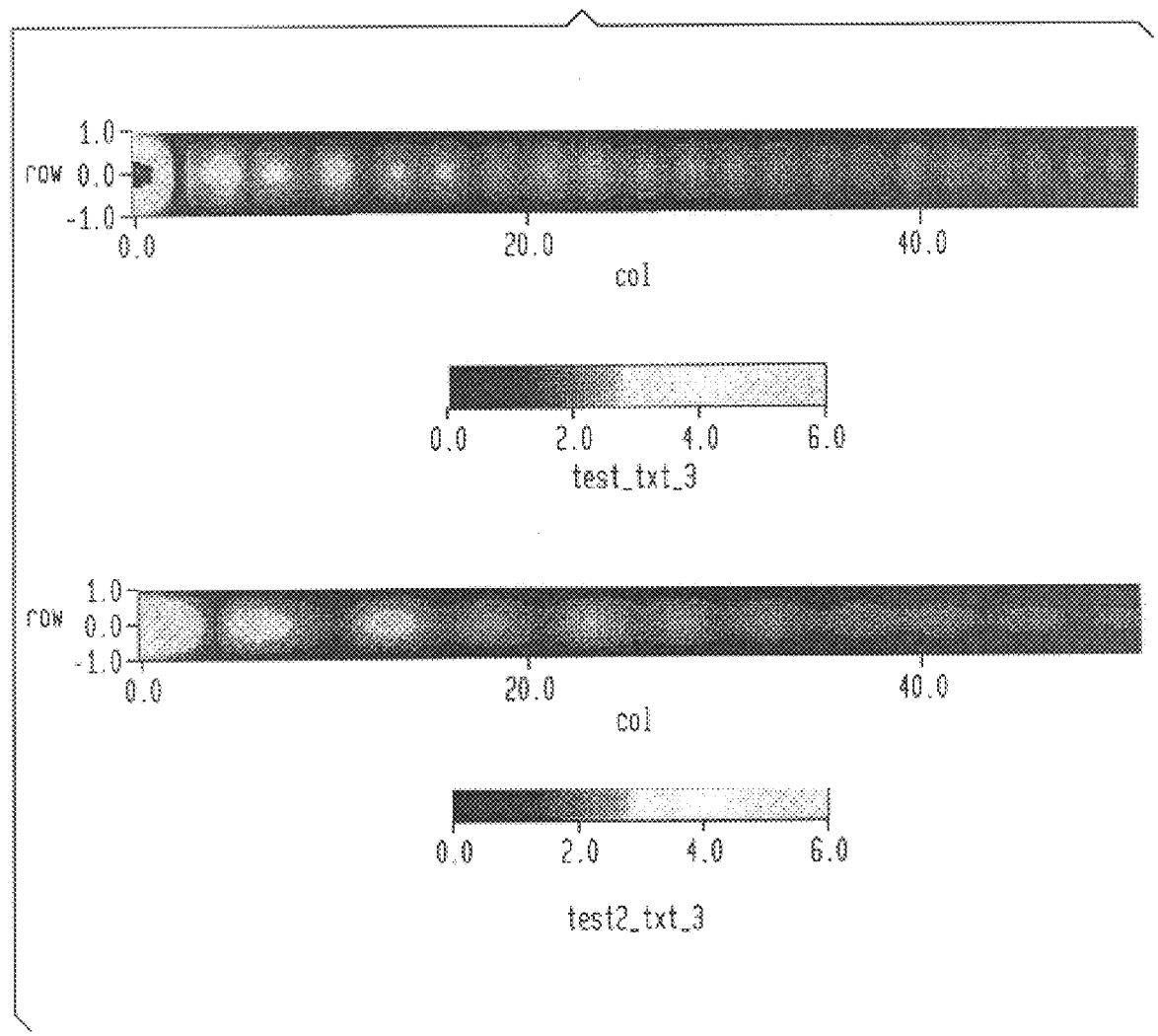
FIG. 11 shows the scattering patter from an ideal 20 micron and an ideal 10 micron filament.
Figure 14:
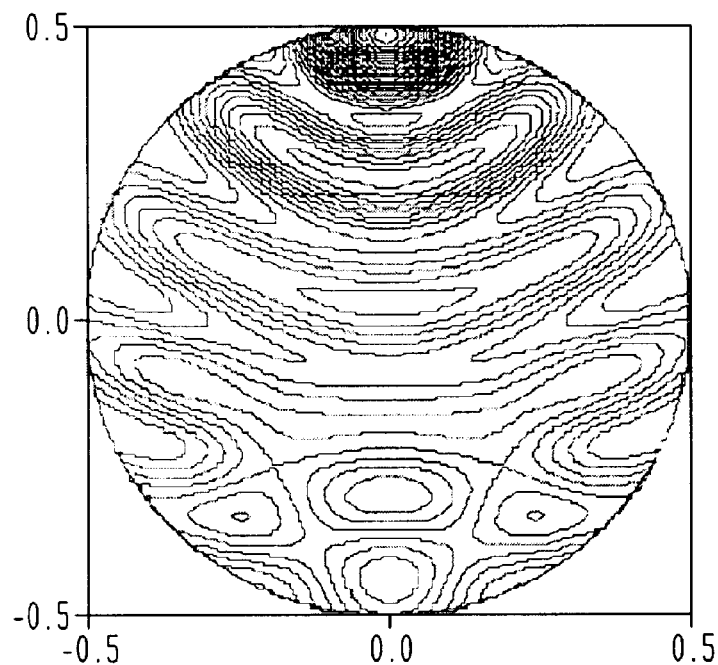
FIG. 14 shows an internal electric field pattern for $\lambda/d=1.58$.
Figure 15:
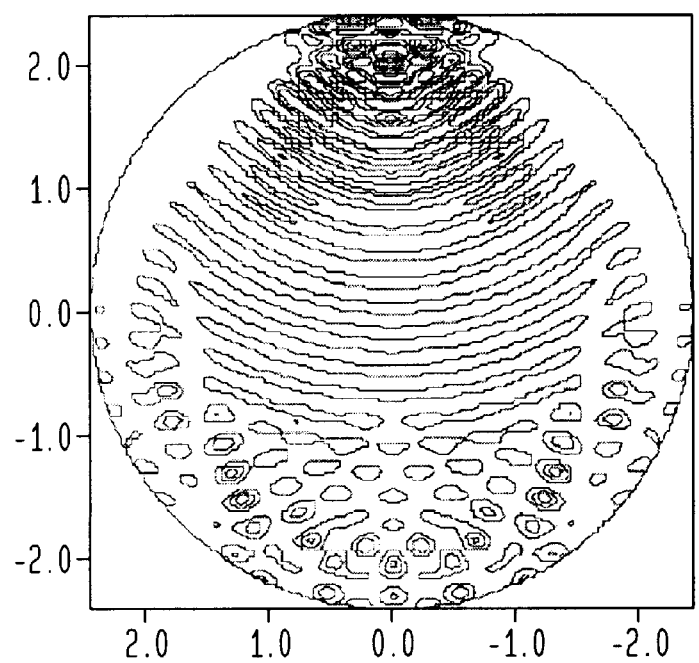
FIG. 15 shows an electric filed pattern for internal electric fields of $\lambda/d=7.9$.
Figure 16:
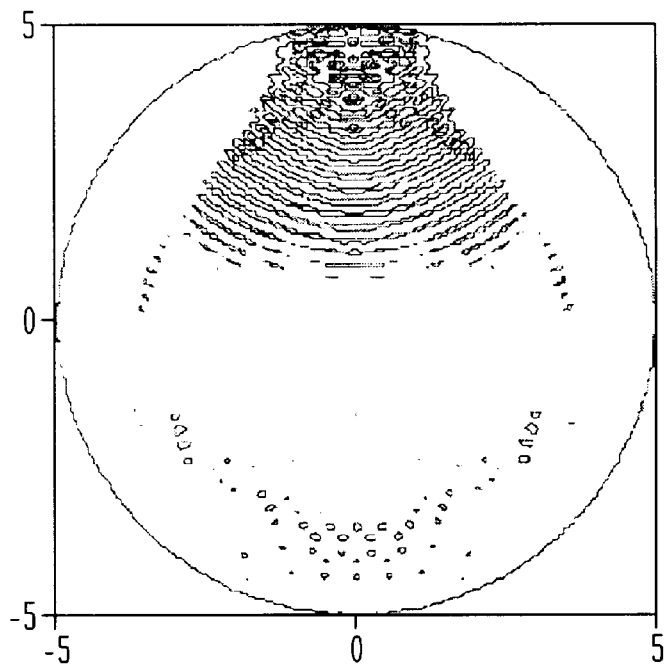
FIG. 16 shows an electric filed pattern for internal electric fields of $\lambda/d=15.8$.
Figure 17:
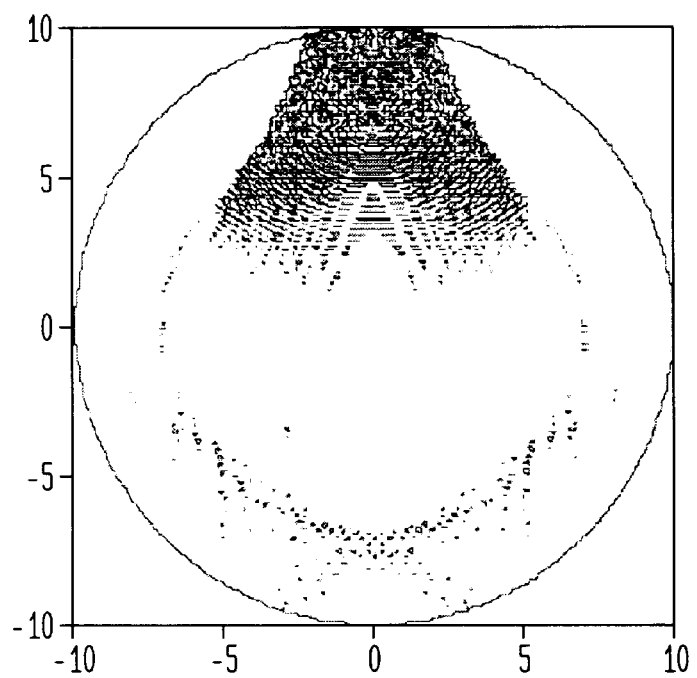
FIG. 17 shows an electric field pattern for internal electric fields of $\lambda/d=31.6$.

Accurate modeling requires solution of Maxwell's equation for propagation of light in the filament. FIGS. 11 and 12 show some typical results from these calculations. Both the forward, side and backscatter patterns can be accurately simulated.

FIG. 12 below shows calculated forward scattering patterns vs angle. Match with observed patterns is good (compare FIG. 5). Filament diameter calculated using the Maxwell solutions agreed with conventional measurements to a precision better than 1%.

Filament diameter can also be obtained from the backscattered patterns. These patterns are also very sensitive to the filament diameter and have been used to calculate filament diameter to an accuracy of a few percent. A typical backscatter pattern is shown below in FIG. 13.

One way to analyze the data is to extract the dominant Fourier component from the data and compare it with the dominant Fourier component from the calculations. Typical results obtained using data similar to the above are described hereinafter.

Solving Maxwell's equation also yields information on internal electric fields. This is important as it determines the region of the filament that is being probed. In essence the region probed is that region which has the highest electric field gradients. FIGS. 14–17 show internal electric field patterns for a variety of probing wavelengths with different rations of probing wavelength to filament diameter. The region probed can be adjusted somewhat by judicious choice of the probing wavelength.

Figure 18:
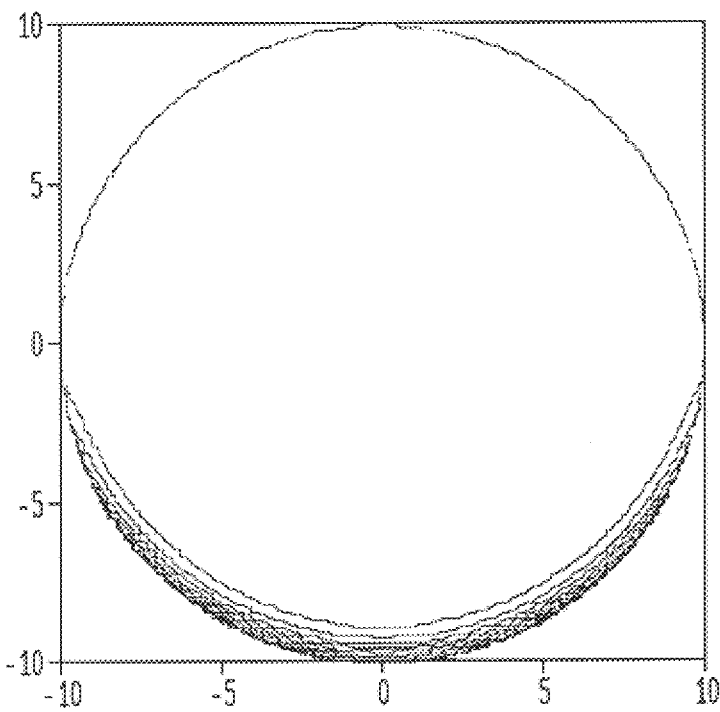
FIG. 18 shows an electric field pattern for internal electric fields of $\lambda/d=31.6$ and $n=(1.5,0.1)$ for a highly absorbing fiber wherein the probe region is limited to a surface layer.

As shown in FIGS. 14–17, the probed region changes with the ratio of the wavelength to filament size. It is also interesting to note that as the ratio of $\lambda/d$ increases, the electric field patterns start to resemble the ray tracing results shown in FIG. 10. This is particularly true of the near focal region of the rays. For highly absorbing fiber the probed region is limited to a surface layer whose depth depends on the absorption coefficient. This is shown in FIG. 18.

Models For Fine Scattering

Figure 19:
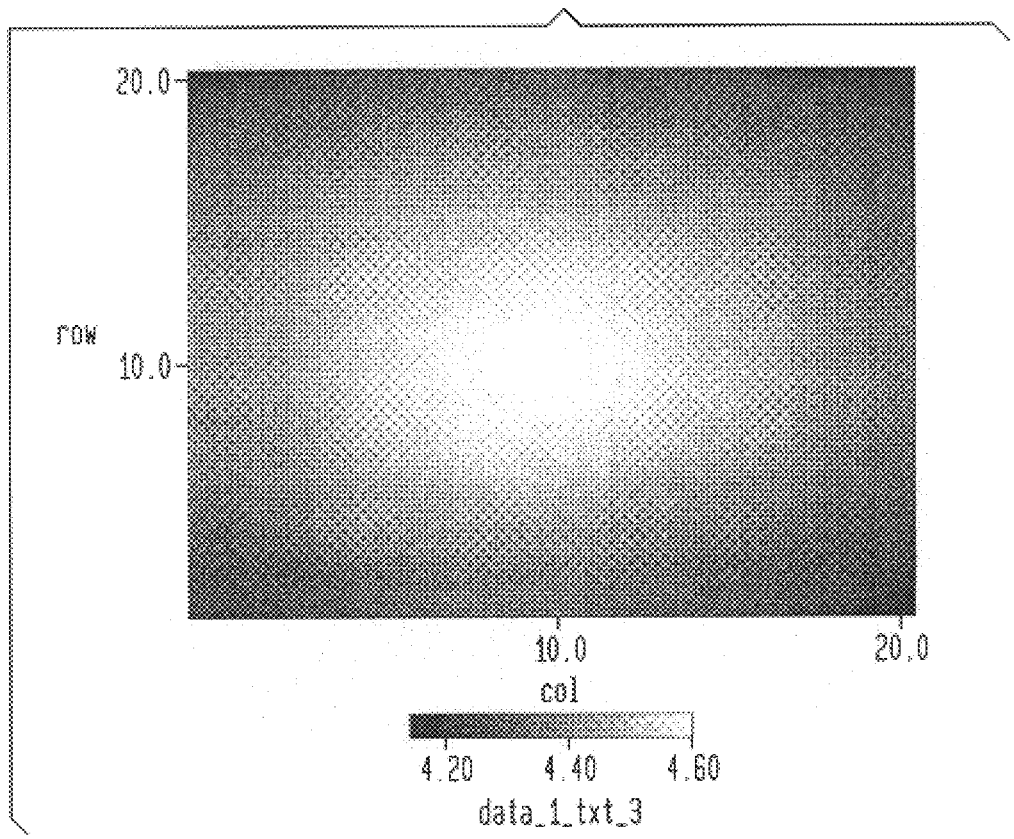
FIG. 19 shows a scattering patter for a very small inhomogeneity.

Up to this point the scattering patterns caused by relatively large scale inhomogeneities have been considered. As shown in FIG. 19, these cause a scattering pattern which lies primarily in the equatorial plane, with little light scattered out of the plane. Only if there are small scale inhomogeneities will there be significant scattering out of the equatorial plane. In the limit where the scattering inhomogeneity is much smaller than the wavelength of the probing light (Rayleigh scattering), the scattering pattern generated by a single (point like) scattering center is shown in FIG. 19 below. This pattern is simply a very broad featureless blob. If this scattering center were located inside a filament, the resulting scattering pattern would be a convolution of this pattern and the spot patterns created by the filament. The net result would be just a blurring out of the patterns as shown in FIG. 11.

Figure 20:
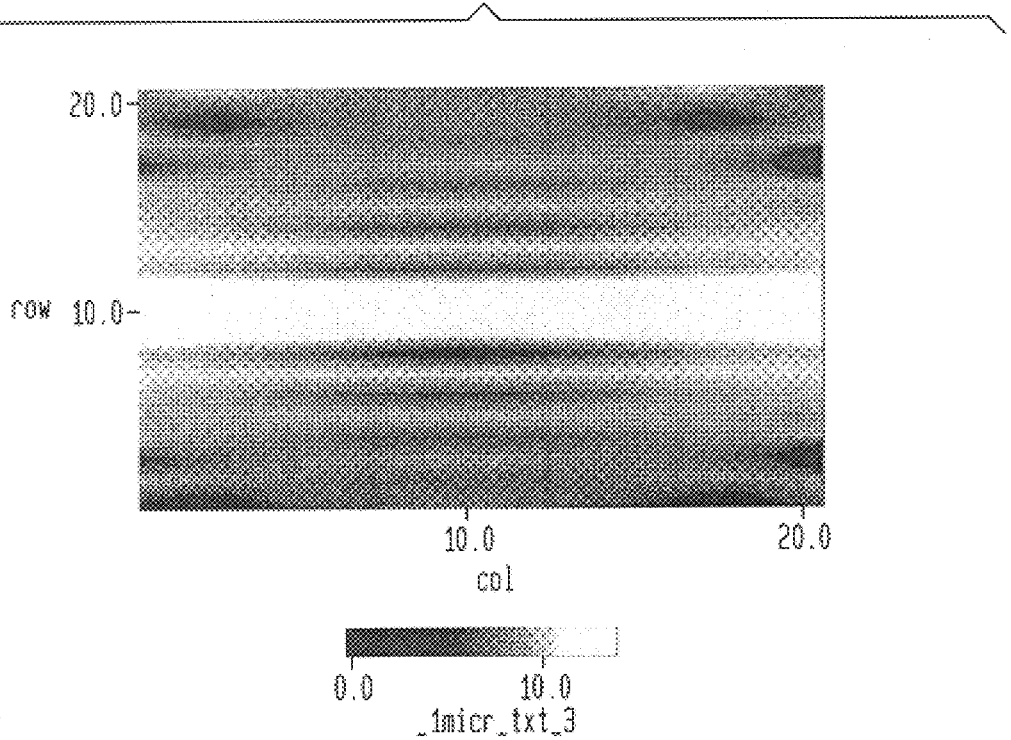
FIG. 20 shows a scattering pattern from a thin 1 micron long structure.

The scattering pattern from single long structure (1 micron in length) is shown in FIG. 20. Here the scattering structure is much thinner than the wavelength but has a vertical extent nearly 2 wavelengths long. Here the detector field is assumed to be flat. As a consequence of a finite longitudinal scattering structure, horizontal bands appear both below and above the primary horizontal band. If the pattern shown in FIG. 17 were now to be convoluted with the spot pattern shown in FIG. 11, we would obtain scattering patterns that would be very close to those observed in FIG. 6.

Figure 21:
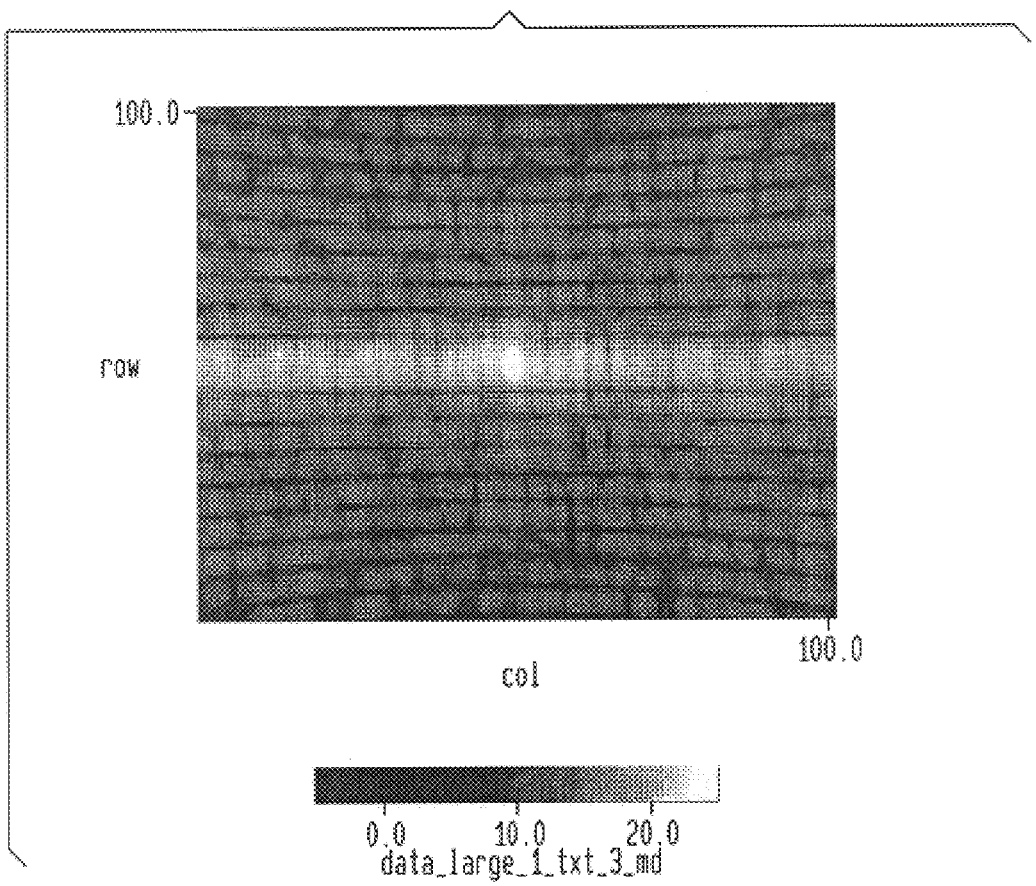
FIG. 21 shows the scattering pattern from many partially correlated 1 micron structures.

If we now calculate the scattering patterns of several thousand such long structures, nearly randomly distributed, and with a correlation length of 1 micron we obtain the pattern shown in FIG. 21. We can now qualitatively reproduce the full patterns that are observed. We see the bright forward scattered peak that is located at the center of the pattern. There is the bright primary horizontal band characteristic of the filament diameter, and a rich horizontal sideband structure that loses correlation with the central band as its distance from the central band increases. All of these observations are similar to those seen in experiments.

Experimental Results

Having developed a satisfactory model, various schemes can be considered to measure parameters of interest.

Transmission Technique

Figure 22:
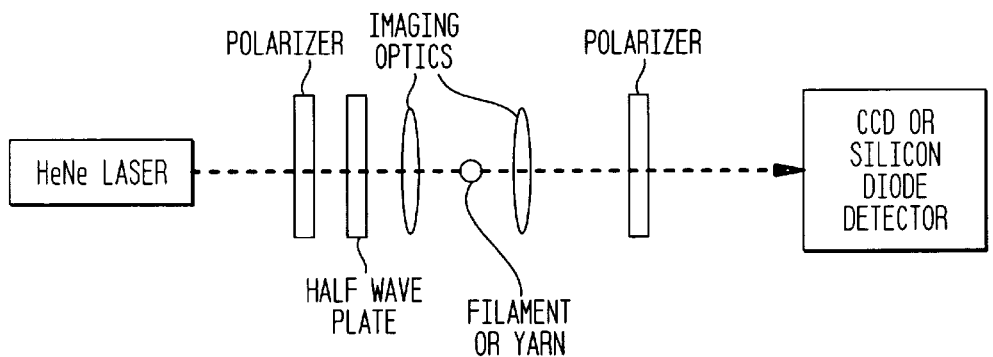
FIG. 22 is a schematic drawing of an experimental set out for transmission of birefringence measurements.

The first scheme to be tried is based on the principle that birefringent materials introduce a phase delay that is polarization dependent. A linearly polarized wave that is incident at an angle to an optical anisotropy will no longer be linearly polarized. A schematic diagram that makes use of this feature to measure birefringence is shown in FIG. 22.

Figure 23:
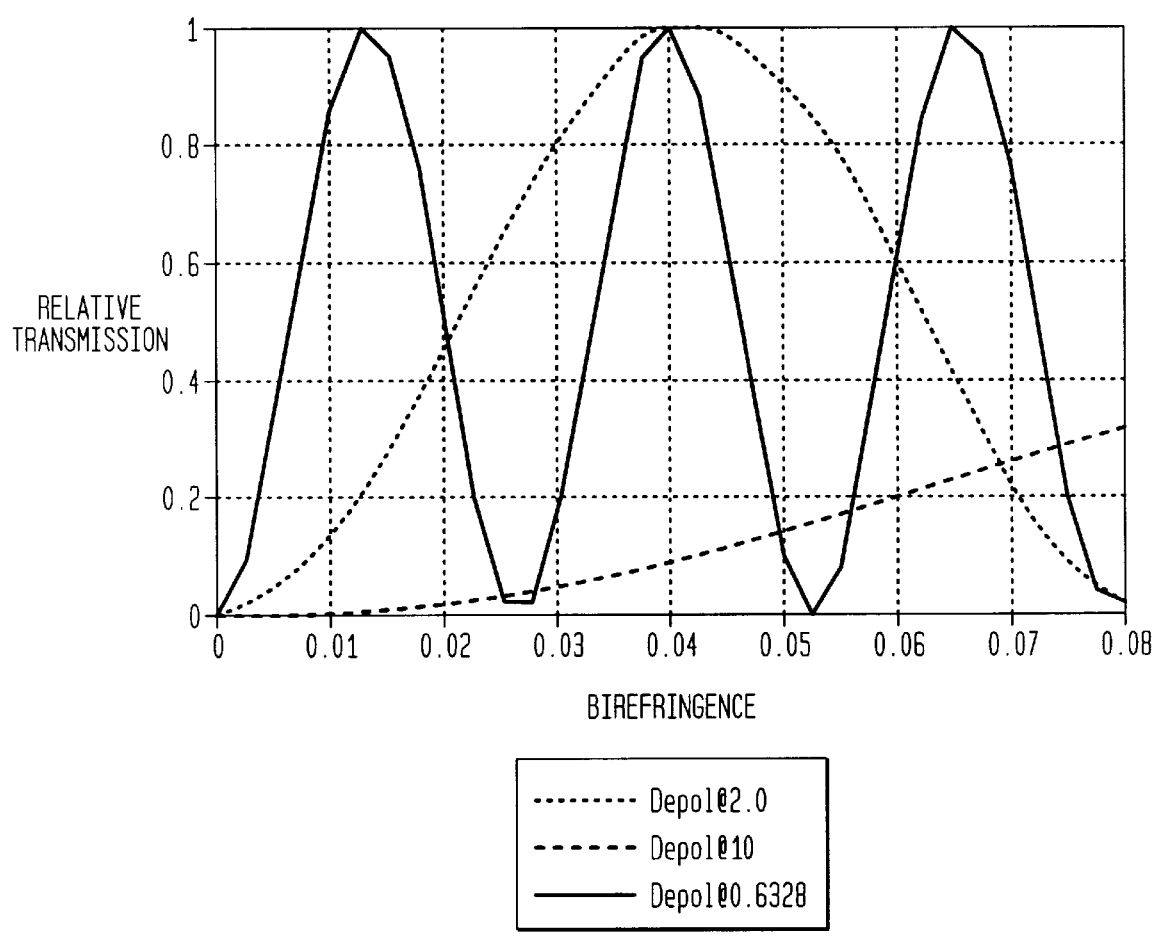
FIG. 23 is a plot of the transmission vs birefringence for various probing wavelengths.

This scheme measures a line integrated effect along a given ray path. As a first good approximation, effective ray paths can be calculated from ray tracing as shown in FIG. 10. With non-birefringent material, there will be no net depolarization of the rays and no transmitted light through the second polarizer. As birefringence increases, there will be increasing depolarization and more light will be transmitted. However, further increases in birefringence will eventually cause the transmitted light to decrease as the phase delay between the two polarizations approaches integer wavelengths. A plot showing this effect, for various probing wavelengths is shown in FIG. 23.

The solid line shows the expected fractional transmission vs birefringence for a 22 micron filament and a probing wavelength of 0.6328 microns. As evident in the FIG. 23, there could be an ambiguity in the birefringence value for a given transmission. This ambiguity can be removed by using two or more different probing wavelengths or a sufficiently long wavelength. For this technique to work the sample must be at least partially transparent. This seemed to be true for all samples tested, even the navy blue samples from CAMAC. However, in the case of some dyes which have a very strong resonance (absorption) at the probing wavelength, this technique may not be useful at that particular wavelength. In any case at least two probing wavelengths are needed to make this technique work as there are two unknown parameters, the birefringence and the filament diameter.

A quantitative calculation of the birefringence requires a knowledge of the filament diameter. Using the filament diameter obtained from density and denier we can plot the expected light transmission as a function of birefringence for a series of fibers. This is shown FIG. 24. The solid line is representative of filaments A-1, A-2, and A-3, the dotted line is representative of filament B-5 and H-5. The accuracy of this measurement depends on the slope of the curves shown at the given birefringence. The accuracy is greatest near the 0.5 value in the transmission coefficient and poorest at the minima and maxima of the curves. This effect is illustrated by the shaded boxes shown near the A-4 and H-5 fibers in FIG. 24.

Figure 25:
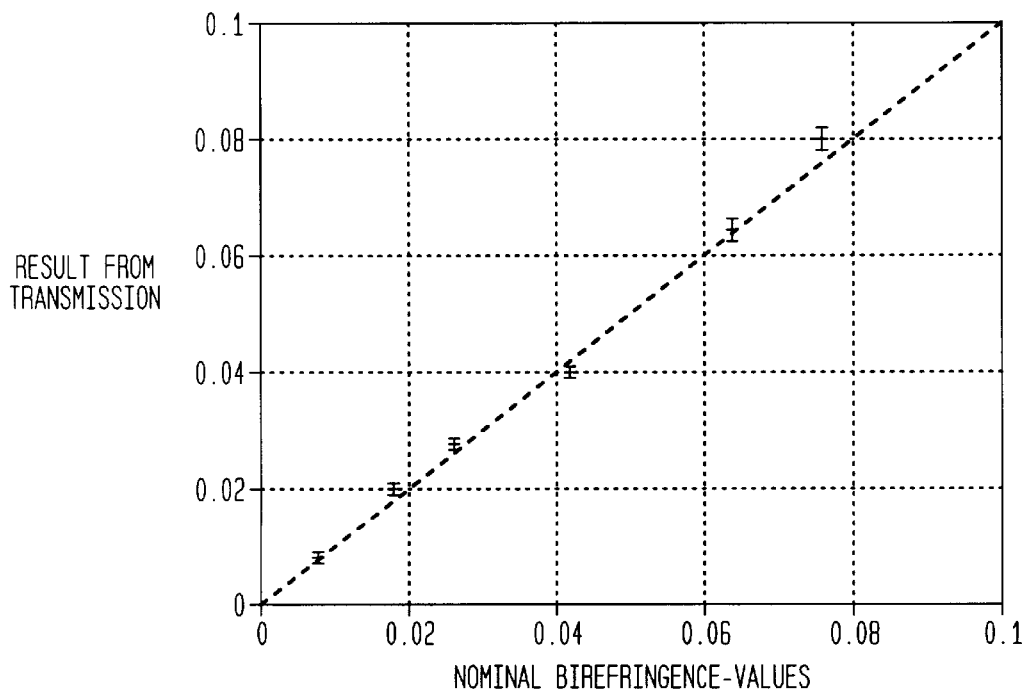
FIG. 25 shows a graph of comparison of birefringence measurements from depolarization measurements vs industry standard technique.

A comparison of the birefringence value obtained using the transmission technique and those obtained from conventional techniques is shown in FIG. 25.

Figure 24:
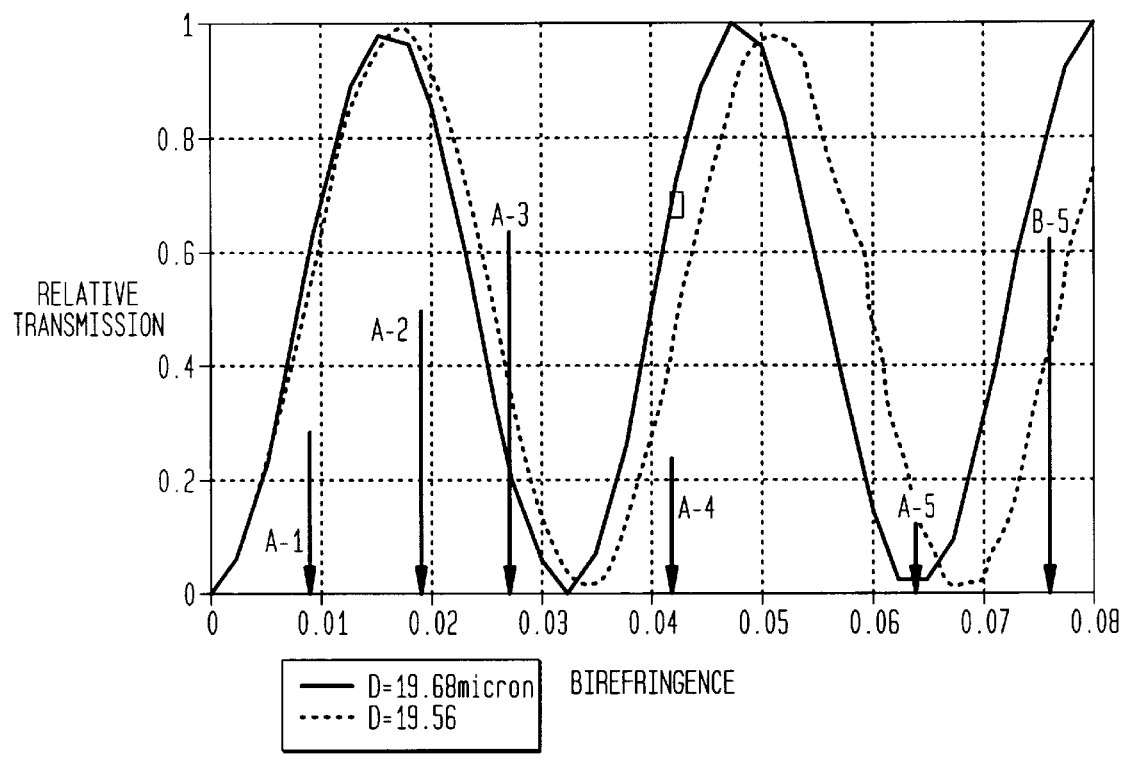
FIG. 24 is a graph of light transmitted through crossed polarizers vs birefringence.

There is excellent agreement between the two measurements. The only point that stands out is the measurement for the B-5 fiber (FIG. 24). The discrepancy could be due to a difference in the filament diameter from the one used in the calculation. An implicit assumption in the interpretation of the transmitted data is that the optical path is identical for rays of both polarizations. At high birefringence value this is no longer the case and a correction must be applied. These correction factors could also account for the observed discrepancy.

This technique is also applicable to non-circular filaments, but it is not obvious if it can be applied to filament bundles or yarns, where the possibility of multiple scattering exists. In tests conducted on PET yarns, it appears that multiple scattering is not fatal to this kind of measurement but this has not been demonstrated.

Side Scattering

As pointed out previously, the spot pattern observed at some angle to the laser beam depends on the filament diameter and the index of refraction. Since the index of refraction measurement is dependent on polarization, it could be used as a means of measuring the birefringence as well as the filament diameter.

Figure 26:
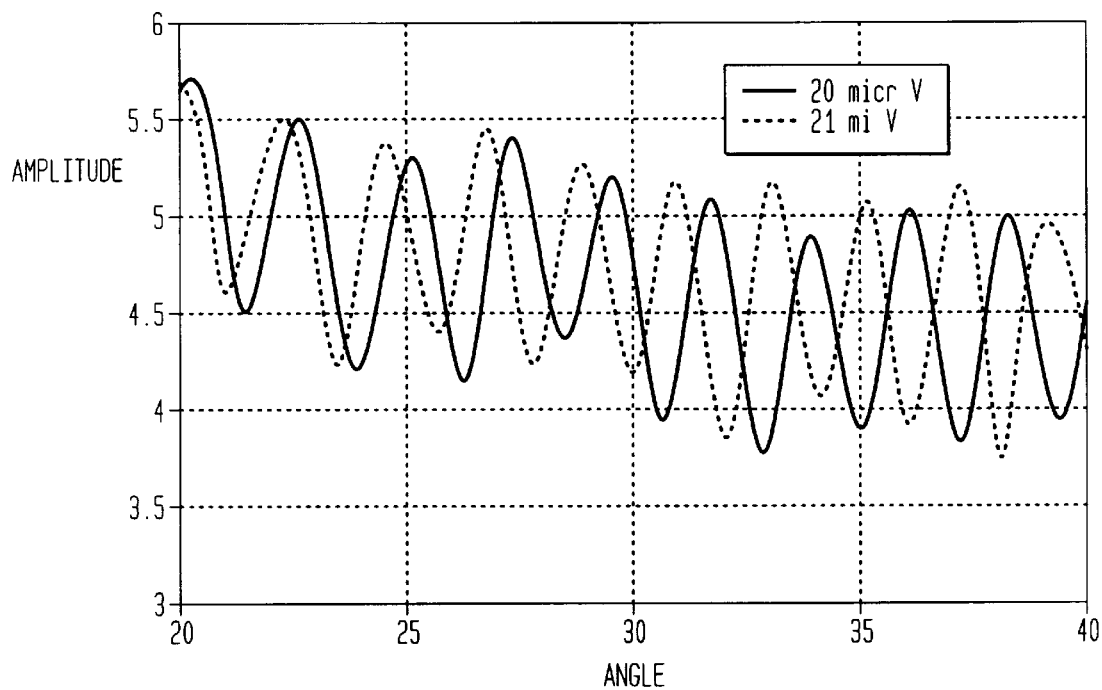
FIG. 26 shows a graph of the effect of filament diameter on spot pattern.

We shall first examine the dependance of the spot pattern on filament diameter. In FIG. 26 the spot pattern for filaments of 20 and 21 microns vs angle is plotted. As can be seen, the period of the pattern is very sensitive to the filament diameter, and the period can thus be used as an accurate measure of the diameter.

Figure 27:
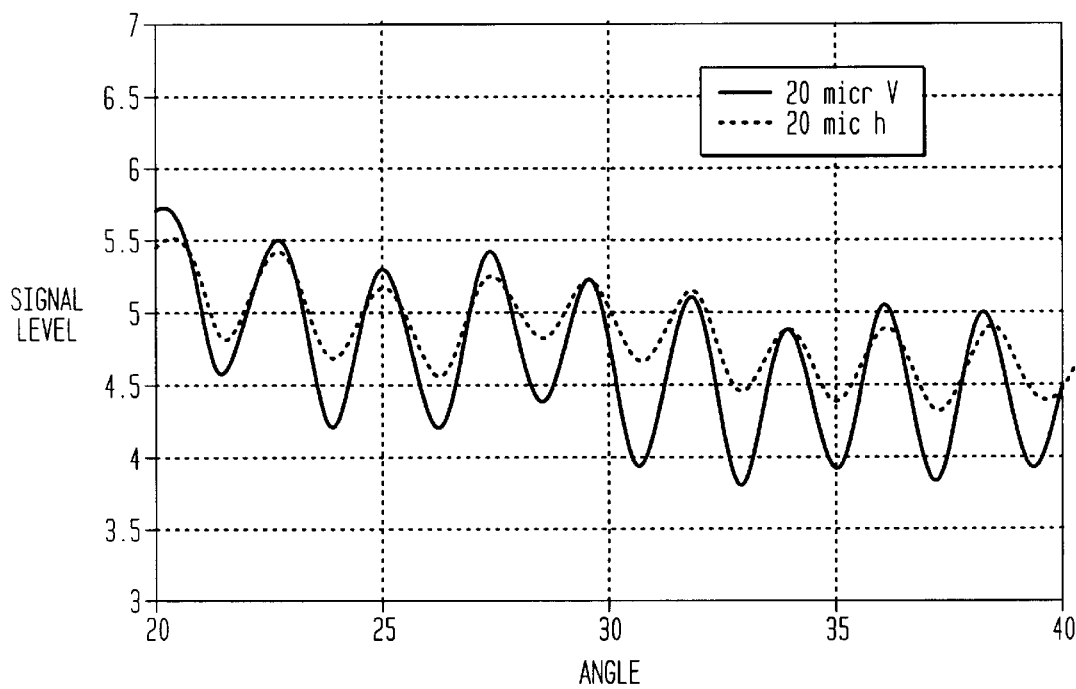
FIG. 27 is a graph of primary spot amplitude vs angle for two polarizations.

Since this pattern is due to the interference of light scattered/reflected from various part of the filament one would not expect this pattern to depend on polarization if the scattering filament is practically isotropic. However, one expects changes in the amplitude, since the reflection coefficient is polarization dependent. It is important to verify and quantify this if change in spot position is to be used as a measure of birefringence. A graph of the scattering pattern for vertical and transverse polarization with respect the filament axis is shown in FIG. 27.

As expected there is no change in the period or position of the peaks for the two orthogonal polarizations.

Figure 28:
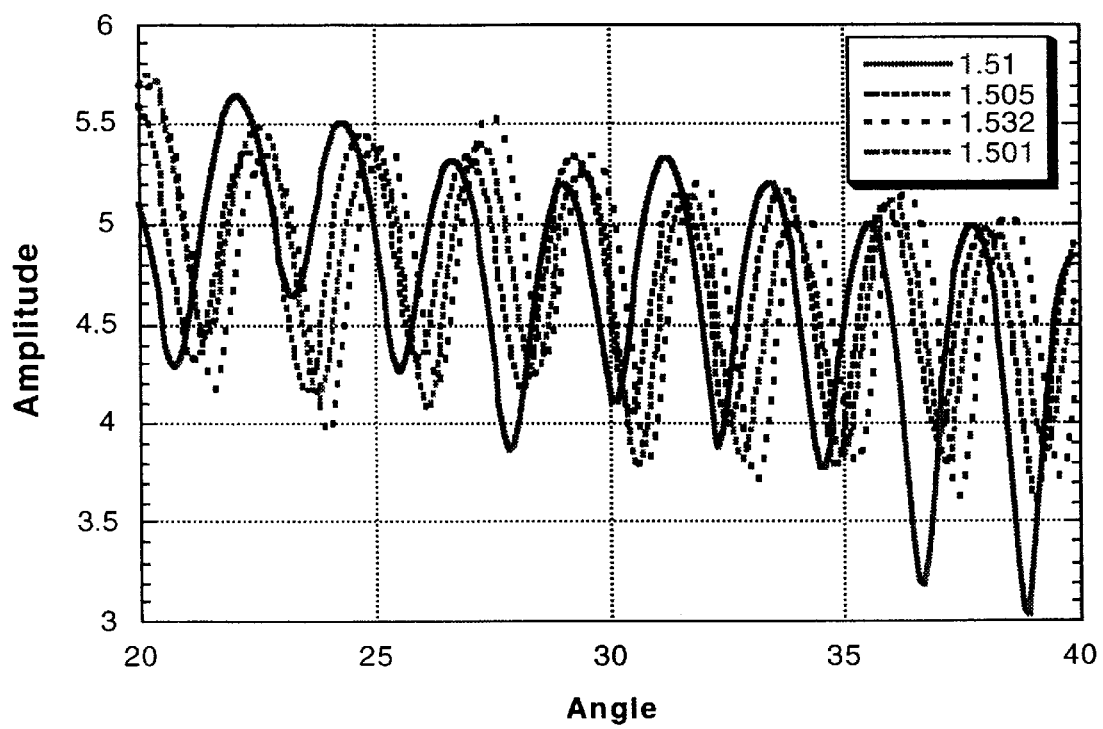
FIG. 28 is a graph showing the effect of birefringence on spot pattern.

For birefringent fibers, the position but not the period of the patterns shifts as the polarization is rotated. In essence one sees the pattern jiggle back and forth as the polarization is changed. The amount of jiggle depends on the birefringence of the material. This has been confirmed experimentally and is shown in FIG. 28.

The advantage of this technique over the previous one is that the filament diameter is directly measured and does not enter as an additional unknown parameter in the measurement. It also lends itself to cost effective implementation through the use of rotating Ronchi rulings and non-imaging detectors. However, this technique is probably not applicable to filament bundles.

Backscatter

Figure 29:
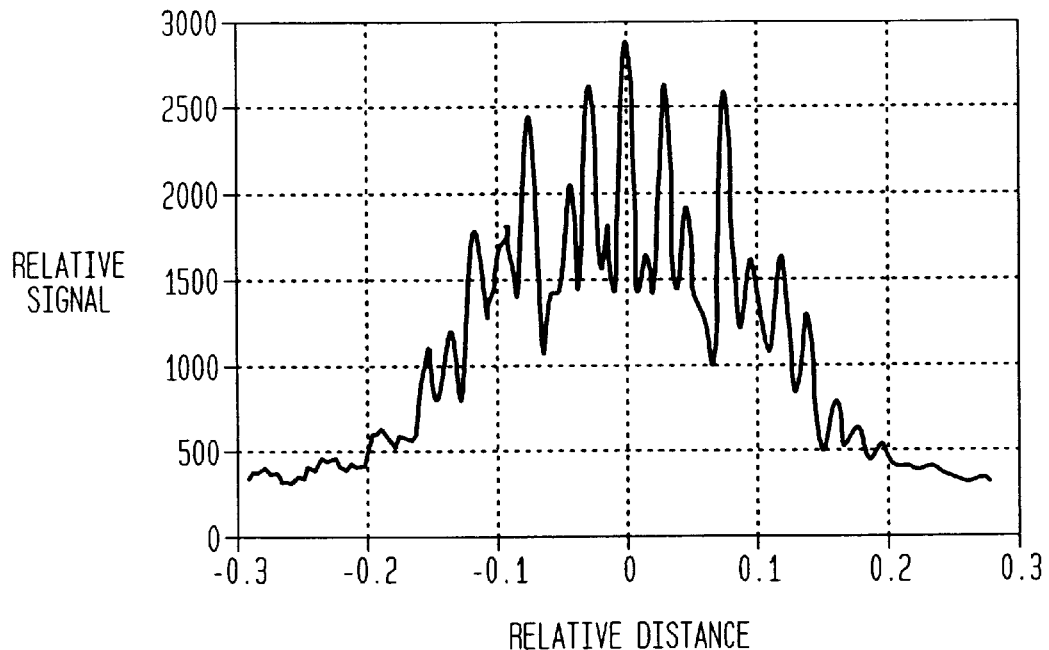
FIG. 29 shows the backscatter pattern from a fiber.

A final technique that was tested is to use the backreflected light as a means of measuring the yarn birefringence and filament diameter. We will first examine the use of the backreflected pattern as a means of measuring the filament diameter. Such a pattern from the A-1 fiber is shown in FIG. 29.

Figure 30:
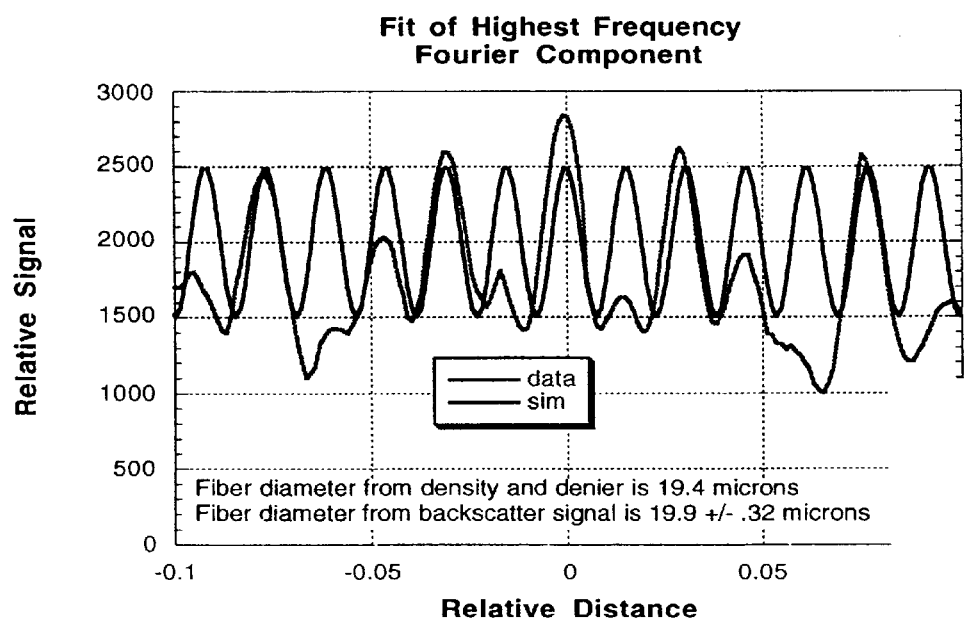
FIG. 30 is a graph of the fit of highest frequency Fourier component of the data shown in FIG. 29.

One can do a crude and quick calculation of the filament diameter by extracting the dominant Fourier component from the above data and then matching it to that obtained from those expected for various filament diameters. The result of such a process is shown in FIG. 30.

Using this relatively simple technique it is possible to obtain measurement which agree to a few percent with those obtained from the denier and density.

Backscatter or Reflection

Figure 31:
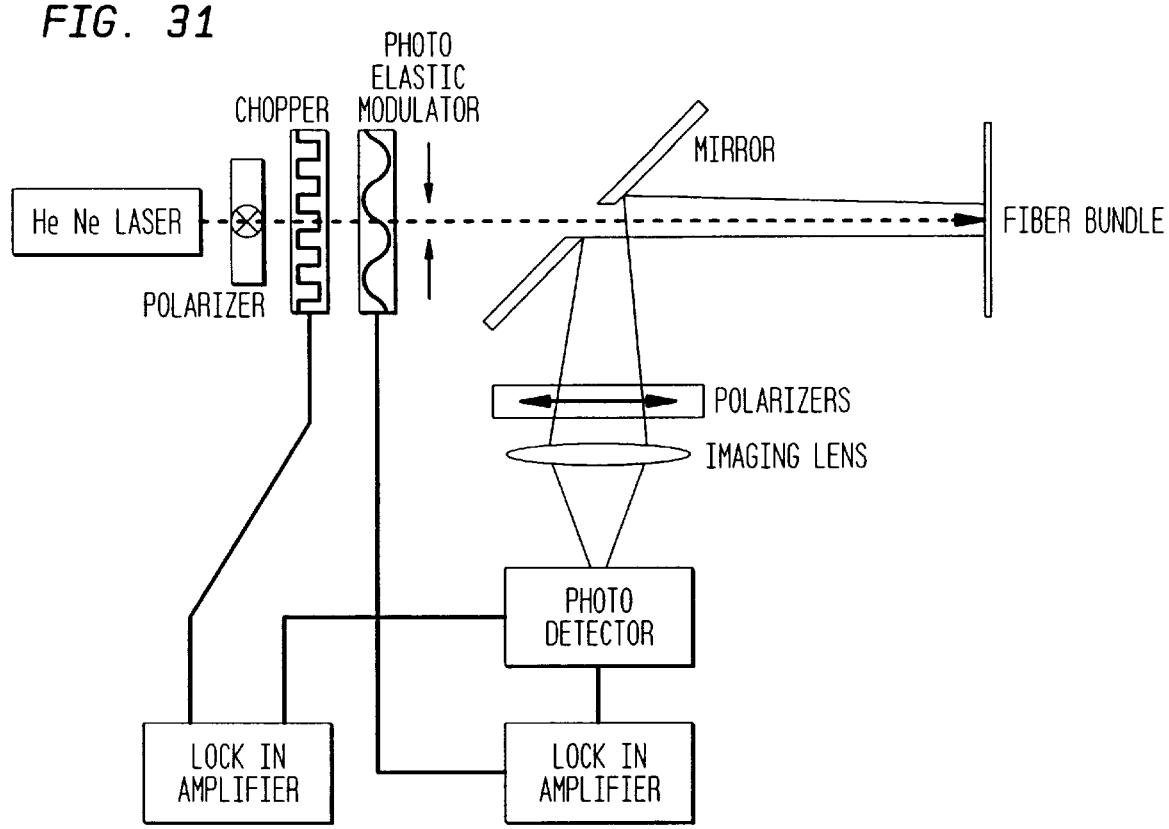
FIG. 31 shows an experimental set up for reflection tests of birefringence.

One can also use the polarization dependence of the reflected light to measure birefringence. For non-birefringent materials the amplitude of specularly reflected light depends weakly on the polarization of the incident rays (reflection perpendicular to a surface). For birefringent materials the reflection is strongly polarization dependent. A schematic of the test setup used to verify this concept is shown in FIG. 31.

Figure 32:
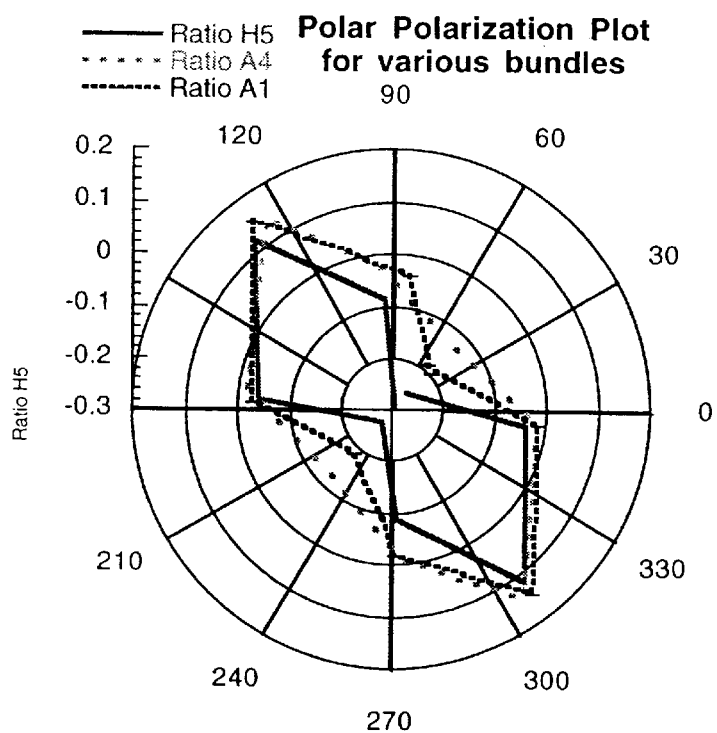
FIG. 32 is a polar polarization plot for various bundles tested by the test set-up of FIG. 31.

Here the light from the incident laser beam is modulated in amplitude by a chopper and polarization modulated with a photo-elastic modulator. This was done to make the measurement amplitude independent, so that the ratio of the signals seen by the two lock-in amplifiers is a measure of the birefringence. A typical result obtained from fiber bundles is shown in FIG. 32. Here the ratio of the signal for varying polarization angle and for three fibers with different degree of birefringence is plotted.

Here the 130–310 degree axis correspond to a polarization aligned perpendicularly to the yarn, whereas the 40–220 axis correspond to a polarization parallel to the yarn. As expected there is little difference in the relative signal for the cross-polarized case and a significant difference for the co-polarized case. As can be seen from FIG. 32, there is a clear difference in the polarization patterns for the three case studies. There are two contributions to the backscattered signal, a dominant one due to specular scatter and one due to multiple scattering or complex bounding around. In addition there are several form factors that go into the instrumental response of the apparatus depicted in FIG. 31. If one assumes that all of these factors remain the same for the various bundles tested and uses the signal from one of the bundles as normalizer, FIG. 33 is obtained.

Figure 33:
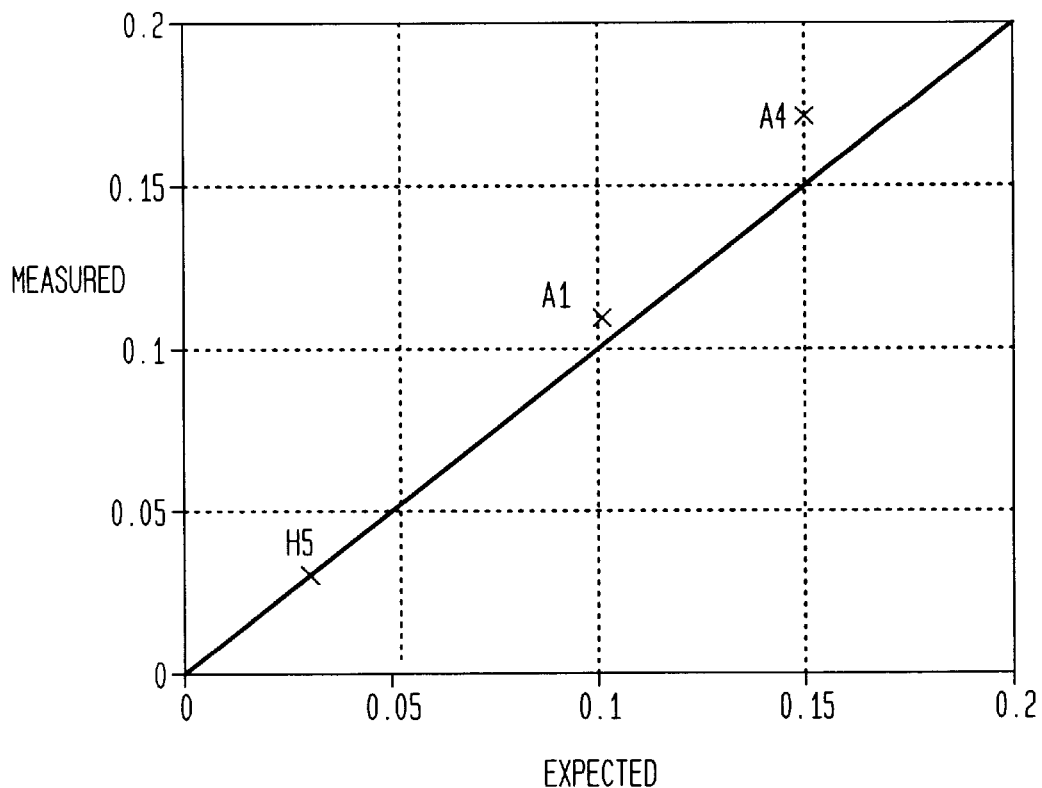
FIG. 33 is a comparison of measured and expected relative modulation levels.

FIG. 33 shows the expected modulation depth vs the measured modulation depth for the three fibers studied. Fiber H-5 was used as the normalizing fiber. For A-4 fiber there is a 12% discrepancy between the measured and expected modulation levels. This translates into a similar uncertainty in the birefringence value. Much more information than was shown or used in the analysis is available from the apparatus in FIG. 31. In particular phase information or the details of the ellipticity of the scattered light carries additional information on non-specular components. This information has not yet been folded into the analysis. Techniques such as correlation interferometry (using broad band sources) and dispersion interferometry will be tested as a way of removing errors due to multiple scattering effects. Finally the use of much longer probing wavelengths (sub mm to mm wavelength) is another technique that would make the interpretation of the backscattering data simpler. These long wavelengths will not be able to resolve the individual filament and thus make bulk measurements over the full bundle.

Computer Interpretation of Data

Computer codes have been developed which can solve for the scattered electromagnetic waves by a specified dielectric body in two dimensions. Fortran codes are written which solve an integral equation for the scattered waves numerically by piece-wise point matching method.

Consider a harmonic wave incident in free space on a two-dimensional dielectric cylinder of arbitray cross sectional shape. The incident wave may be a TM or TE mode. The dielectric cylinder is assumed to have the same permeability as free space ($\mu=\mu_0$). The dielectric material is assumed to be linear and isotropic but it may be inhomogeneous with respect to the spatial coordinates:

$$\epsilon=\epsilon(x,y)$$

whereas $\epsilon$ represents the complex permittivity.

Let E represent the total electric field intensity; that is, the field generated by the source in the presence of the dielectric cylinder. The scattered field $E^S$ is defined to be the difference between the total and the incident fields. Thus $$E=E^i+E^S$$

From Maxwell's equations for a dielectric body, the scattered field may be considered generated by a equivalent electric current radiating in unbounded free space, where the current density is given by $$J=j\omega(\epsilon-\epsilon_0)E$$

with $\omega$ representing the angular frequency $2\pi f$.

It is well-known that the field of an electric current filament dI parallel to the z axis in free space given by $$dE^S=-z(\omega\mu/4)H_0^{(2)}(k\rho)dI$$

where $H_0^{(2)}(k\rho)$ is the second kind Hankel function of order zero, $\rho$ is the distance from the current filament to the observation point and $k=2\pi/\lambda$ where $\lambda$ is the free space wavelength.

The current filament which generates the scattered field is given by $$dI=JdS=j\omega(\epsilon-\epsilon_0)E\ dS.$$

The scattered field is given by $$E^S(x,y)=-(jk^2/4)\Sigma\Sigma(\epsilon_r-1)E(x',y')H_0^{(2)}(k\rho)dx'dy'$$

where (x,y) and (x,y) are the coordinates of the observation point and the source point, $\epsilon_r$ is the complex relative dielectric constant, $\epsilon/\epsilon_0$.

The integral equation for the total field is then given by $$E(x,y)+(jk^2/4)\Sigma\Sigma(\epsilon_r-1)E(x',y')H_0^{(2)}(k\rho)dx'dy'=E^i(x,y)$$

which can be solved numerically by point matching technique.

EXAMPLES

Several examples have been tested using the codes developed. They are: (1) cylindrical shell, (2) cylindrical half-shell, (3) a slab, and (4) three-wing structure. The echo width which represents the scattered field at infinity defined by $$W(\phi)=\text{limit } 2\pi\rho_0|E^S/E^i|^2$$

is plotted as a function of scattering angle $\phi$.

Extension to Three Dimensions

Surface integral equation approach:

$$g(r,r')=exp(-jk|r-r'|)/4\pi|r-r'|$$

$$E(r) = T\int_v + T\int_\Sigma [gn'\times(\nabla'\times E) + (n'\times E)\times\nabla' g + (n'\cdot E)\nabla' g]ds'$$

-continued $$H(r) = T\int_v + T\int_\Sigma [gn' \times (\nabla' \times H) + (n' \times H) \times \nabla' g + (n' \cdot H)\nabla' g]ds'$$

The birefringence is measured just inside the fiber. The longer the wavelength, the larger percentage of the bulk of the object that is being read.

Computer Interpretation of Data

A computer program to solve Maxwell's equations in connection with the determination of birefringence of a fiber has been developed. Two dimensional scattering of the ion waves by the dielectric textile fibers of an arbitray cross-section involves integral equations which are solved numerically to determine the scattered field by the known scatterers. The scattering object is treated as a single hollow cylindrical fiber.

Basically the program solves the integral equations formed from Maxwell's formulations, describing the scattered laser beam. The deviration of the equations contained within the program are set forth in the reference field communication by *Moment Methods* by Roger F. Harrington, IEE Press, 1992. Initially, the program defines values that are known and/or Constance. The particular fiber for which the program is designed is a hollow fiber and accordingly, the shell width and the shell made ratios are defined. Importantly, the computer program can be extended to cover fibers of other shapes. Then, using the parameters initially defined, the integral equations for the incident electric field and scattering matrix are defined. The integral equations are solved in the do loops. A library sub-routine is used to invert the matrix. Descriptions of the library sub-routines employed in the program are attached behind the program. This computer program will be run with a wide variety of parameters to get results. Then the experimental data can be compared to the results to determine fiber properties. Another approach that can be taken is that instead of an integral equation approach, is an Eigen function approach, which is based on a different mathematical model which will give better results for a fiber having a circular cross-section. The integral equation approach will be best for trilobal shapes.

Trilobal Shapes

Figure 34:
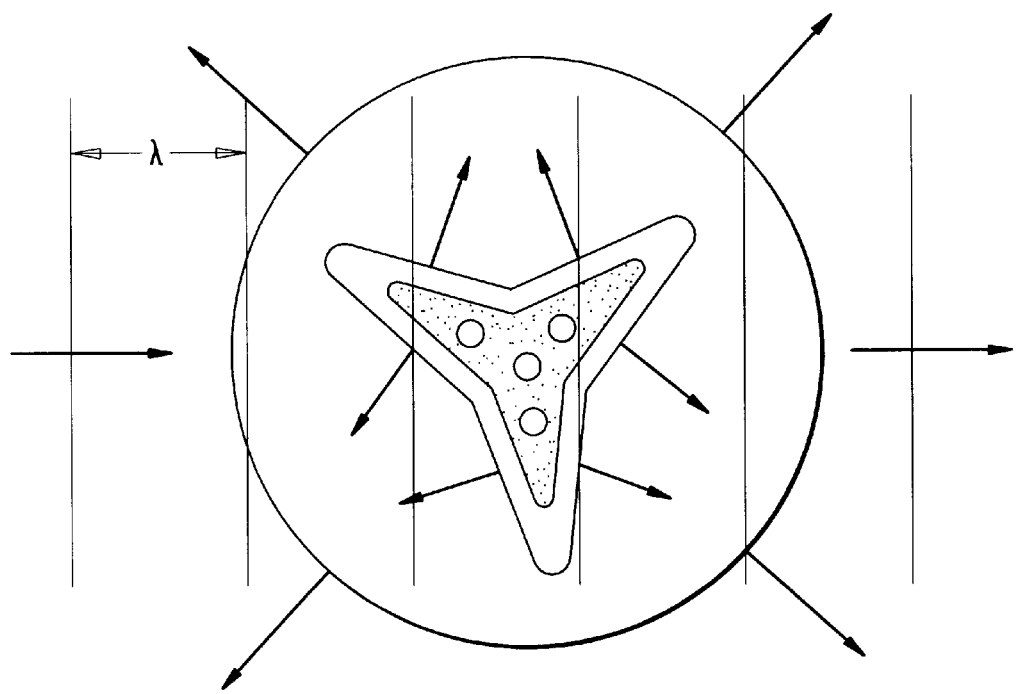
FIG. 34 is a cross-sectional view of a trilobal fiber.

Often fibers are not cylindrical but can be trilobal. See FIG. 34. Importantly, trilobals have a size on the order of 20 microns to 2 millimeters. A $CO_2$ laser has a wavelength of approximately 10 microns which is on the order of the size of the trilobal. It may be desirable to use two lasers of different wavelengths or to provide one laser with different chopper frequencies, in order to accurately work with trilobal fibers.

Having thus described the invention in detail, it is to be understood that the foregoing description is not intended to limit the spirit and scope thereof What is desired to be protected by Letters Patent is set forth in the appended claims.

What is claimed is:

1. An apparatus for measuring birefringence of a moving or static polymer strand during production of the polymer comprising:

laser means for emitting a laser beam directed at the polymer strand, the laser means penetrating the polymer strand and then backscattering therefrom;

modulation means for modulating the laser means;

collection means for collecting forward backscatter from the polymer strand;

beam splitter means for splitting the backscatter into first and second signals;

detector means for receiving first and second signals from the beam splitter; and computer means interconnected with the modulation means and the detector means for calculating birefringence.

2. The apparatus of claim 1 wherein the laser means, beam splitter, collection means and detection means are contained within a housing and the collection means collects forward backscatter from the polymer strand.

3. The apparatus of claim 1 wherein beam splitter means splits the backscatter into at least three signals with polarization analyzers.

4. The apparatus of claim 3 wherein at least three signals are at 0, 45 and 90 degrees.

5. The apparatus of claim 1 further comprising means for conditioning a laser beam emitted by the laser means.

6. The apparatus of claim 5 wherein the means for conditioning the laser beam comprises a polarizer.

7. The apparatus of claim 5 wherein the means for conditioning the laser beam comprises a chopper.

8. The apparatus of claim 7 wherein a synchronous detection system is interconnected with the detection means.

9. The apparatus of claim 3 wherein the beam splitter means splits the backscatter into additional signals.

10. The apparatus of claim 9 wherein the detector means comprises additional detectors for detecting the additional signals.

11. A method of determining birefringence of a moving polymer strand during production comprising:

directing a laser beam at the polymer strand;

penetrating the polymer strand with the laser beam;

sampling an interior portion the polymer strand with the laser beam;

backscattering the laser beam from the polymer strand;

collecting the backscatter from the polymer strand;

detecting the backscatter; and calculating the birefringence with a computer.

12. The method of claim 11 wherein the step of calculating the birefringence comprises solving integral equations based on Maxwell's formulas.

13. The method of claim 11 wherein the step of calculating the birefringence comprises solving eigenvalue formulas.

14. The method of claim 11 further comprising the step of conditioning the laser beam by polarizing the laser beam.

15. The method of claim 11 further comprising the step of conditioning the laser beam by modulating the laser beam in amplitude and polarization angle.

16. The method of claim 11 wherein the polymer strand comprises a bundle of polymer strands and birefringence of the bundle is determined.

17. A method of measuring micro structures of a moving polymer strand during production comprising:

directing a laser beam at a polymer strand;

allowing the laser beam to penetrate the polymer strand;

scattering the laser beam from the polymer strand;

collecting the scattered light;

analyzing the scattered light;

calculating a value from the scattered light;

utilizing the calculated value to determine properties of the polymer strand.

18. The method of claim 17 further comprising the step of conditioning the laser beam by polarizing the laser beam.

19. The method of claim 17 further comprising the step of conditioning the laser beam by modulating the laser beam in amplitude and polarization.

20. The method of claim 17 wherein the step of collecting the scattered light comprises spitting the scattered light into three signals with polarization analyzers at 0, 45 and 90 degrees.

21. The method of claim 17 wherein the laser beam comprises at least two different wavelengths for removing degeneracy in the measurements.

22. The method of claim 21 further comprising using backscatter from the at least two different wavelengths to calculate birefringence and strand diameter.

* * * * *